(12) United States Patent
Drake et al.

(10) Patent No.: US 11,504,536 B2
(45) Date of Patent: Nov. 22, 2022

(54) METHOD AND APPARATUS FOR ATRIAL EVENT DETECTION

(71) Applicant: Medtronic, Inc., Minneapolis, MN (US)

(72) Inventors: Ronald A. Drake, St. Louis Park, MN (US); Melissa G. T. Christie, Ham Lake, MN (US); Kathryn Hilpisch, Cottage Grove, MN (US); Bushan K. Purushothaman, Plymouth, MN (US); William Schindeldecker, Foreston, MN (US)

(73) Assignee: Medtronic, Inc., Minneapolis, MN (US)

( * ) Notice: Subject to any disclaimer, the term of this patent is extended or adjusted under 35 U.S.C. 154(b) by 179 days.

(21) Appl. No.: 16/587,871

(22) Filed: Sep. 30, 2019

(65) Prior Publication Data

US 2020/0101297 A1 Apr. 2, 2020

Related U.S. Application Data

(60) Provisional application No. 62/739,530, filed on Oct. 1, 2018.

(51) Int. Cl.
*A61N 1/365* (2006.01)
*A61N 1/375* (2006.01)

(52) U.S. Cl.
CPC ..... *A61N 1/36585* (2013.01); *A61N 1/36521* (2013.01); *A61N 1/36542* (2013.01); *A61N 1/3756* (2013.01); *A61N 1/37512* (2017.08)

(58) Field of Classification Search
CPC ............ A61N 1/36585; A61N 1/36521; A61N 1/3756; A61N 1/37512; A61N 1/36542
See application file for complete search history.

(56) References Cited

U.S. PATENT DOCUMENTS

| | | |
|---|---|---|
| 4,485,813 A | 12/1984 | Anderson |
| 5,052,388 A | 10/1991 | Sivula |
| 5,507,782 A | 4/1996 | Kieval |
| 5,593,431 A | 1/1997 | Sheldon |
| 5,683,432 A | 11/1997 | Goedeke |
| 5,885,471 A | 3/1999 | Ruben |
| 6,044,297 A | 3/2000 | Sheldon |

(Continued)

FOREIGN PATENT DOCUMENTS

EP 3260166 A1 12/2017

OTHER PUBLICATIONS (PCT/US2019/053962) PCT Notification of Transmittal of the International Search Report and the Written Opinion of the International Searching Authority, dated Dec. 18, 2020, 10 pages.

*Primary Examiner* — George R Evanisko

(57) ABSTRACT

An intracardiac ventricular pacemaker includes a pulse generator for delivering ventricular pacing pulses, an impedance sensing circuit, and a control circuit in communication with the pulse generator and the impedance sensing circuit. The pacemaker is configured to produce an intraventricular impedance signal, detect an atrial systolic event using the intraventricular impedance signal, set an atrioventricular pacing interval in response to detecting the atrial systolic event, and deliver a ventricular pacing pulse in response to the atrioventricular pacing interval expiring.

13 Claims, 10 Drawing Sheets

(56) References Cited

U.S. PATENT DOCUMENTS

| | | |
|---|---|---|
| 6,278,894 B1 | 8/2001 | Salo |
| 6,539,261 B2 | 3/2003 | Dal Molin |
| 6,604,002 B2 | 8/2003 | Dal Molin |
| 7,228,174 B2 | 6/2007 | Burnes |
| 7,570,990 B2 | 8/2009 | Faber |
| 7,689,283 B1 | 3/2010 | Schecter |
| 7,908,002 B2 | 3/2011 | Hoijer |
| 8,239,011 B2 | 8/2012 | Li |
| 8,380,308 B2 | 2/2013 | Rosenberg et al. |
| 8,433,409 B2 | 4/2013 | Johnson |
| 8,532,785 B1 | 9/2013 | Crutchfield |
| 8,541,131 B2 | 9/2013 | Lund |
| 8,639,328 B2 | 1/2014 | Hettrick |
| 9,399,140 B2 | 7/2016 | Cho |
| 9,433,792 B2 | 9/2016 | Rosenberg |
| 9,724,518 B2 | 8/2017 | Sheldon |
| 9,775,982 B2 | 10/2017 | Grubac |
| 2012/0089032 A1 | 4/2012 | Park |
| 2012/0109245 A1* | 5/2012 | Hettrick ............... A61N 1/3684 607/25 |
| 2012/0184859 A1 | 7/2012 | Shah |
| 2016/0250478 A1 | 9/2016 | Greenhut et al. |
| 2017/0368346 A1* | 12/2017 | Muessig ............... A61N 1/3622 |
| 2018/0085588 A1 | 3/2018 | Splett |
| 2018/0085589 A1 | 3/2018 | Splett |
| 2018/0117337 A1 | 5/2018 | Demmer |
| 2018/0154154 A1 | 6/2018 | Sheldon |
| 2018/0161580 A1 | 6/2018 | Demmer |
| 2019/0167972 A1* | 6/2019 | Stahmann ............ A61N 1/3756 |

\* cited by examiner

METHOD AND APPARATUS FOR ATRIAL EVENT DETECTION

CROSS-REFERENCE TO RELATED APPLICATION

This application claims the benefit of U.S. Provisional Application Ser. No. 62/739,530, filed Oct. 1, 2018, the entire content of which is incorporated herein by reference.

TECHNICAL FIELD

This disclosure relates to an implantable medical device and method for detecting atrial events using an intraventricular impedance signal.

BACKGROUND

Implantable cardiac pacemakers are often placed in a subcutaneous pocket and coupled to one or more transvenous medical electrical leads carrying pacing and sensing electrodes positioned in the heart. A cardiac pacemaker implanted subcutaneously may be a single chamber pacemaker coupled to one transvenous medical lead for positioning electrodes in one heart chamber, atrial or ventricular, or a dual chamber pacemaker coupled to two transvenous leads for positioning electrodes in both an atrial and a ventricular chamber. Multi-chamber pacemakers are also available that may be coupled to three leads, for example, for positioning electrodes for pacing and sensing in one atrial chamber and both the right and left ventricles.

Leadless intracardiac pacemakers are available or have been proposed that are implantable within a ventricular chamber of a patient's heart for delivering ventricular pacing pulses. Such a pacemaker may sense R-wave signals attendant to intrinsic ventricular depolarizations and deliver ventricular pacing pulses in the absence of sensed R-waves. While single chamber ventricular sensing and pacing by an intracardiac ventricular pacemaker may adequately address some patient conditions, some patients may benefit from atrial and ventricular (dual chamber) sensing for providing atrial-synchronized ventricular pacing in order to maintain a more normal heart rhythm.

SUMMARY

The techniques of this disclosure generally relate to a pacemaker configured to produce an intraventricular impedance signal for use in sensing atrial events. Atrial events may be sensed directly from the intraventricular impedance signal for controlling atrial synchronized ventricular pacing in some examples. In other examples, the intraventricular impedance signal may be used in establishing atrial event sensing parameters used in sensing the atrial event from another signal and/or for confirming atrial event sensing from another signal, e.g., from an intraventricular motion signal produced by an accelerometer.

In one example, the disclosure provides an intracardiac ventricular pacemaker including a pulse generator, an impedance sensing circuit, and a control circuit in communication with the impedance sensing circuit and the pulse generator. The pulse generator is configured to generate and deliver ventricular pacing pulses to a patient's heart via electrodes coupled to the pacemaker. The impedance sensing circuit is configured to produce an intraventricular impedance signal. The control circuit is configured to detect an atrial systolic event using the intraventricular impedance signal, set an atrioventricular pacing interval in response to detecting the atrial systolic event and control the pulse generator to deliver a ventricular pacing pulse upon expiration of the atrioventricular pacing interval.

In another example, the disclosure provides a method performed by an intracardiac ventricular pacemaker. The method includes producing an intraventricular impedance signal by an impedance sensing circuit, detecting an atrial systolic event by a control circuit of the pacemaker using the intraventricular impedance signal, setting an atrioventricular pacing interval by the control circuit in response to detecting the atrial systolic event; and delivering a ventricular pacing pulse upon expiration of the atrioventricular pacing interval.

In another example, the disclosure provides a non-transitory, computer-readable storage medium comprising a set of instructions which, when executed by a control circuit of an intracardiac ventricular pacemaker, cause the pacemaker to produce an intraventricular impedance signal, detect an atrial systolic event using the intraventricular impedance signal, set an atrioventricular pacing interval in response to detecting the atrial systolic event and deliver a ventricular pacing pulse upon expiration of the atrioventricular pacing interval.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

The techniques disclosed herein provide a method for sensing atrial events by a ventricular pacemaker, which may be an intracardiac pacemaker wholly implantable within a ventricular heart chamber. In general, this disclosure describes techniques for atrial event sensing using an intraventricular impedance signal by an implantable medical device. As described below, an atrial systolic event, sometimes referred to as the "atrial kick," may be detected from an impedance signal acquired from an electrode pair that is implanted in the ventricle of a patient's heart. Atrial events can be detected from within the ventricle for controlling the timing of atrial synchronized ventricular pacing pulses. Atrial-synchronized ventricular pacing pulses can be delivered by a pacemaker implanted in the ventricle without requiring electrodes or another sensor outside the ventricle, e.g., in or on the atria of the patient's heart or elsewhere in the patient's body, for detecting atrial events. In this way, the operation of a pacemaker, e.g., a leadless intraventricular pacemaker, can be improved by promoting reliable, accurate atrial event sensing and thereby enabling atrial synchronized ventricular pacing.

Achieving reliable atrial event sensing and atrial synchronized ventricular pacing by an intraventricular pacemaker is a technological challenge because atrial signals, such as electrical P-wave signals, are relatively low amplitude signals compared to ventricular signals, especially when sensed from within a ventricle. The techniques disclosed herein address this technological challenge by generating an intraventricular impedance signal and using the intraventricular impedance signal in atrial event sensing to promote more reliable and accurate atrial event sensing. Enabling atrial synchronized ventricular pacing through reliable atrial event sensing improves the pacing function of the pacemaker because ventricular pacing accurately synchronized to sensed atrial events promotes a more normal heart rhythm compared to pacing the ventricles asynchronously with the atria, e.g., in a patient experiencing atrioventricular (AV) conduction block. Atrial synchronized ventricular pacing augments the hemodynamic benefit of ventricular pacing by accurately timing ventricular pacing pulses (and subsequent ventricular contraction) following the atrial contribution to ventricular filling compared to asynchronous ventricular pacing or poorly timed ventricular pacing pulses due to unreliable atrial event sensing, e.g., oversensing or undersensing of atrial events.

Figure 1:
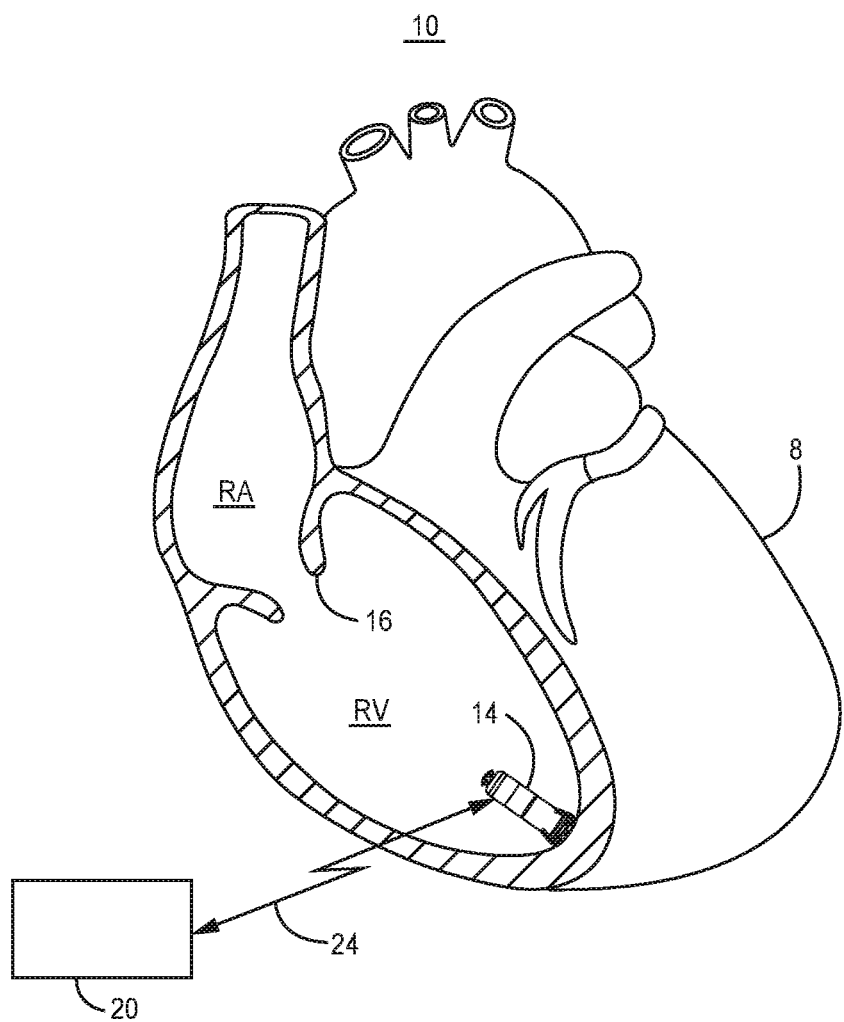
FIG. 1 is a conceptual diagram illustrating an intracardiac ventricular pacing system that may be used to sense cardiac signals and deliver pacing therapy to a patient's heart.

FIG. 1 is a conceptual diagram illustrating an intracardiac ventricular pacing system 10 that may be used to sense cardiac signals and deliver pacing therapy to a patient's heart 8. The cardiac signals may include electrical signals corresponding to the electrical depolarization of the myocardium, intraventricular impedance signals correlated to changes in blood volume in the heart over a cardiac cycle, and intraventricular motion signals induced by cardiac motion and flowing blood. IMD system 10 includes an intracardiac ventricular pacemaker 14 and an external device 20 used to transmit data to and receive data from pacemaker 14.

Pacemaker 14 may be a transcatheter intracardiac pacemaker which is adapted for implantation wholly within a heart chamber, e.g., wholly within the right ventricle (RV) or wholly within the left ventricle (LV) of heart 8 for sensing cardiac signals and delivering ventricular pacing pulses. Pacemaker 14 is generally reduced in size compared to subcutaneously implanted pacemakers and may be generally cylindrical in shape to enable transvenous implantation via a delivery catheter.

Pacemaker 14 is capable of producing electrical stimulation pulses, e.g., pacing pulses, delivered to heart 8 via electrodes on the outer housing of the pacemaker. Pacemaker 14 may be a leadless pacemaker that is configured to sense a cardiac electrical signal using housing based electrodes for producing a ventricular electrogram (EGM) signal. The cardiac electrical signals may be sensed using the housing-based electrodes that are also used to deliver pacing pulses to the right ventricle (RV), in the position shown. The housing-based electrodes may be used to produce an intraventricular impedance signal, which is correlated to the electrical impedance of the blood volume surrounding the housing-based electrodes when positioned within a heart chamber. A drive current signal may be injected using the housing based-electrodes and the resultant voltage signal may be sensed by the housing-based electrodes to produce the intraventricular impedance signal. Alternatively, a drive voltage signal may be applied across by the housing-based electrodes and the resultant current signal may be sensed for producing the intraventricular impedance signal.

Pacemaker 14 is shown positioned in the RV, along an endocardial wall, e.g., near the RV apex though other locations are possible. The techniques disclosed herein are not limited to the pacemaker location shown in the example of FIG. 1 and other positions within heart 8 are possible. For example, intracardiac ventricular pacemaker 14 may be positioned in the LV and configured to detect cardiac signals, including intraventricular impedance signals, and deliver atrial-synchronized ventricular pacing to the LV using the techniques disclosed herein. Pacemaker 14 may be positioned within the RV or LV to provide respective right ventricular or left ventricular pacing and for sensing cardiac signals within the ventricular chamber for controlling the timing of the ventricular pacing pulses.

Pacemaker 14 is configured to control the delivery of ventricular pacing pulses to the RV in a manner that promotes synchrony between atrial contraction and ventricular contraction, e.g., by maintaining an AV interval between atrial events and ventricular pacing pulses. That is, pacemaker 14 controls pacing pulse delivery to maintain a desired AV interval between atrial contractions corresponding to atrial systole and ventricular pacing pulses delivered to cause ventricular depolarization and ventricular systole. The AV interval may be a default value or a programmed value selected by a clinician and is the time interval from the detection of the atrial event until delivery of the ventricular pacing pulse.

According to the techniques described herein, the intraventricular impedance signal is used in detecting atrial systolic events that produce the active ventricular filling phase or atrial "kick." In some instances, the atrial systolic event may be detected by pacemaker 14 directly from the intraventricular impedance signal or a derivative signal of the intraventricular impedance signal. In other instances, the intraventricular impedance signal is used in detecting atrial systolic events by confirming atrial events that are sensed from a different cardiac signal and/or by using the intraventricular impedance signal in establishing sensing parameters for controlling sensing of the atrial systolic event from another cardiac signal.

For example, atrial systolic events may be sensed from a motion signal produced by a motion sensor, such as an accelerometer enclosed by the housing of pacemaker 14. The acceleration of blood flowing into the RV through the tricuspid valve 16 between the right atrium (RA) and RV caused by atrial systole may be detected by pacemaker 14 from the signal produced by an accelerometer included in pacemaker 14. The motion signal produced by an accelerometer implanted within a ventricular chamber includes motion signals caused by ventricular and atrial events and may include non-cardiac signals caused by physical activity and movement of the patient. As described in greater detail below, the intraventricular impedance signal may be used for confirming atrial systolic events sensed from the motion signal and/or adjusting sensing parameters used for sensing atrial systolic events from the motion signal to avoid oversensing other motion signals as the atrial systolic event. For example, one challenge in reliably sensing atrial events from a motion signal may arise during physical activity of the patient that causes patient physical activity signals to be present in the motion signal, which may interfere with the atrial event signal.

Atrial P-waves that are attendant to atrial depolarization are relatively low amplitude signals in the near-field ventricular cardiac electrical signal received by pacemaker 14 (e.g., compared to the near-field R-wave). P-waves, therefore, can be difficult to reliably detect from the cardiac electrical signal acquired by pacemaker 14 implanted in a ventricular chamber. Atrial-synchronized ventricular pacing by pacemaker 14 or other functions that rely on atrial sensing may not be reliable when based solely on a cardiac electrical signal received by pacemaker 14. Atrial event sensing from the intraventricular motion signal may be difficult at times, e.g., due to increased patient physical activity contributing to the motion signal. According to the techniques disclosed herein, pacemaker 14 includes an impedance sensing circuit for producing an impedance signal used for detecting atrial events and/or confirming atrial events sensed from another cardiac signal, e.g., the cardiac electrical signal or the motion signal. Ventricular pacing pulses may be synchronized to the atrial event that is detected directly from the impedance signal, which may include determining a derivative of the impedance signal, by setting a programmable AV pacing interval that controls the timing of the ventricular pacing pulse relative to the detected atrial systolic event. In other examples, detection of the atrial systolic event used to synchronize ventricular pacing pulses to atrial systole may include detection of atrial systolic events from the motion signal or from the cardiac electrical signal with confirmation of the atrial systolic event detection using the impedance signal, which may occur on a periodic or triggered basis.

Pacemaker 14 may be capable of bidirectional wireless communication with external device 20 for programming the AV pacing interval and other pacing control parameters as well as atrial event sensing parameters, which are utilized for detecting atrial systolic events from a selected signal. Aspects of external device 20 may generally correspond to the external programming/monitoring unit disclosed in U.S. Pat. No. 5,507,782 (Kieval, et al.), hereby incorporated herein by reference in its entirety. External device 20 is often referred to as a "programmer" because it is typically used by a physician, technician, nurse, clinician or other qualified user for programming operating parameters in pacemaker 14. External device 20 may be located in a clinic, hospital or other medical facility. External device 20 may alternatively be embodied as a home monitor or a handheld device that may be used in a medical facility, in the patient's home, or another location. Operating parameters, including sensing and therapy delivery control parameters, may be programmed into pacemaker 14 using external device 20.

External device 20 is configured for bidirectional communication with implantable telemetry circuitry included in pacemaker 14. External device 20 establishes a wireless communication link 24 with pacemaker 14. Communication link 24 may be established using a radio frequency (RF) link such as BLUETOOTH®, Wi-Fi, Medical Implant Communication Service (MICS) or other communication bandwidth. In some examples, external device 20 may include a programming head that is placed proximate pacemaker 14 to establish and maintain a communication link 24, and in other examples external device 20 and pacemaker 14 may be configured to communicate using a distance telemetry algorithm and circuitry that does not require the use of a programming head and does not require user intervention to maintain a communication link. An example RF telemetry communication system that may be implemented in system 10 is generally disclosed in U.S. Pat. No. 5,683,432 (Goedeke, et al.), hereby incorporated herein by reference in its entirety. External device 20 may display data and information relating to pacemaker functions to a user for reviewing pacemaker operation and programmed parameters as well as EGM signals, motion sensor signals, impedance signals or other physiological signals generated and transmitted by pacemaker 14 or other physiological data that is determined by and retrieved from pacemaker 14 during an interrogation session.

It is contemplated that external device 20 may be in wired or wireless connection to a communications network via a telemetry circuit that includes a transceiver and antenna or via a hardwired communication line for transferring data to a centralized database or computer to allow remote management of the patient. Remote patient management systems including a centralized patient database may be configured to utilize the presently disclosed techniques to enable a clinician to review EGM, motion sensor signal, impedance signal and marker channel data and authorize programming of sensing and therapy control parameters in pacemaker 14, e.g., after viewing a visual representation of EGM, motion sensor signal, impedance signal, and marker channel data.

Figure 2:
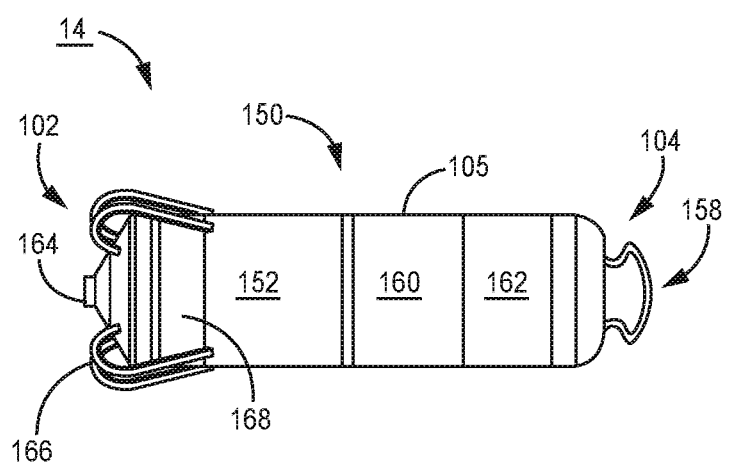
FIG. 2 is a conceptual diagram of the intracardiac pacemaker shown in FIG. 1.

FIG. 2 is a conceptual diagram of the intracardiac pacemaker 14 shown in FIG. 1. Pacemaker 14 includes electrodes 162 and 164 spaced apart along the housing 150 of pacemaker 14 for sensing cardiac electrical signals and delivering pacing pulses. Housing 150 includes a distal end 102 defining a distal-facing surface of pacemaker 14, a proximal end 104 defining a proximal-facing surface of pacemaker 14, and an exterior sidewall 105 extending from the distal end 102 to the proximal end 104. Distal end 102 is referred to as "distal" in that it is expected to be the leading end as pacemaker 14 is advanced through a delivery tool, such as a catheter, and placed against a targeted pacing site within the heart. Exterior, lateral sidewall 105 defines the circumferential or peripheral lateral surface of pacemaker 14. Electrode 164 is shown as a tip electrode located on distal end 102 of pacemaker 14, and electrode 162 is shown as a ring electrode along a mid-portion of sidewall 105, for example adjacent proximal end 104 and wholly or at least partially circumscribing sidewall 105.

Electrodes 162 and 164 form an anode and cathode pair for bipolar cardiac pacing and cardiac electrical signal sensing. Electrodes 162 and 164 may be, without limitation, titanium, platinum, iridium or alloys thereof and may include a low polarizing coating, such as titanium nitride, iridium oxide, ruthenium oxide, platinum black among others. Electrode 164 may serve as a cathode electrode and be coupled to internal circuitry, e.g., a pacing pulse generator, cardiac electrical signal sensing circuitry, and impedance sensing circuit enclosed by housing 150, via an electrical feedthrough crossing housing 150. Electrode 162, defined by an electrically conductive portion of housing 150, serves as a return anode during pacing and sensing. In addition to delivering cardiac pacing pulses and sensing cardiac electrical signal, electrodes 162 and 164 may be used for delivering an impedance drive signal and sensing the resultant raw impedance signal. Electrodes 162 and 164 may be positioned at locations along pacemaker 14 other than the locations shown. For example, electrode 162 may be positioned more proximally or more distally along housing 150 and/or cathode electrode 164 may be a ring electrode on or near the distal end 102 of pacemaker 14.

In other examples, pacemaker 14 may include two or more ring electrodes and/or a proximal tip electrode at proximal end 104 for use in a recording electrode pair for receiving a raw impedance signal resulting from the injected impedance drive signal. In some instances, the relative proximity or degree of contact between electrode 164 and the endocardial surface of the ventricular chamber may vary with cardiac motion, implant position and other factors. Variation in the proximity or degree of contact between tip electrode 164 and the myocardial surface and resulting relative immersion in the ventricular blood pool over a cardiac cycle may cause variation in the raw signal acquired using distal tip electrode 164 for producing an intraventricular impedance signal. As such, in some examples, a second ring electrode, e.g., distal ring electrode 168, may be provided on the lateral sidewall 105 for use with proximal ring electrode 162 for producing an intraventricular impedance signal. When more than two electrodes are available, the same or a different electrode pair may be used for injecting the drive signal and for receiving the resultant raw impedance signal. The intraventricular impedance signal produced by pacemaker 14 from a raw signal received between two spaced apart recording electrodes on lateral sidewall 105 may be more reliable for use in detecting atrial events than an intraventricular impedance signal produced from a raw signal received using electrode 164 on housing distal end 102 as a recording electrode. This greater reliability of the impedance signal may be associated with a more consistent immersion in the surrounding blood volume of two ring electrodes on the peripheral sidewall compared to a distal tip electrode that may have varying contact with myocardial tissue over the cardiac cycle.

Electrode 168 may be coupled to an impedance sensing circuit enclosed by housing 150 via an electrical conductor and may serve as the cathode electrode for injecting a drive current (or voltage) signal and receiving the resultant voltage (or current) signal. Electrode 162 is electrically isolated from electrode 168 and coupled to the impedance sensing circuit via an electrical conductor to serve as the return anode electrode.

Housing 150 is formed from a biocompatible material, such as a stainless steel or titanium alloy. In some examples, the housing 150 may include an insulating coating. Examples of insulating coatings include parylene, urethane, PEEK, or polyimide among others. The entirety of the housing 150 may be insulated, but only electrodes 162, 164 and 168 uninsulated. Electrodes 162 and 168 may be formed as a conductive portion of housing 150 defining a ring electrode that is electrically isolated from the other portions of the housing 150 and from each other. In other examples, the entire periphery of the housing 150 may function as a single electrode that is electrically isolated from tip electrode 164, instead of providing a localized ring electrode such as anode electrode 162.

The housing 150 includes a control electronics subassembly 152, which houses the electronics for sensing cardiac signals, producing pacing pulses and controlling therapy delivery and other functions of pacemaker 14 as described below in conjunction with FIG. 3. Housing 150 further includes a battery subassembly 160, which provides power to the control electronics subassembly 152. Battery subassembly 160 may include features of the batteries disclosed in commonly-assigned U.S. Pat. No. 8,433,409 (Johnson, et al.) and U.S. Pat. No. 8,541,131 (Lund, et al.), both of which are hereby incorporated by reference herein in their entirety.

Pacemaker 14 may include a set of fixation tines 166 to secure pacemaker 14 to patient tissue, e.g., by actively engaging with the ventricular endocardium and/or interacting with the ventricular trabeculae. Fixation tines 166 are configured to anchor pacemaker 14 to position electrode 164 in operative proximity to a targeted tissue for delivering therapeutic electrical stimulation pulses. Numerous types of active and/or passive fixation members may be employed for anchoring or stabilizing pacemaker 14 in an implant position. Pacemaker 14 may include a set of fixation tines as disclosed in commonly-assigned U.S. Pat. No. 9,775,982 (Grubac, et al.), hereby incorporated herein by reference in its entirety.

Pacemaker 14 may optionally include a delivery tool interface 158. Delivery tool interface 158 may be located at the proximal end 104 of pacemaker 14 and is configured to connect to a delivery device, such as a catheter, used to position pacemaker 14 at an implant location during an implantation procedure, for example within a heart chamber.

Figure 3:
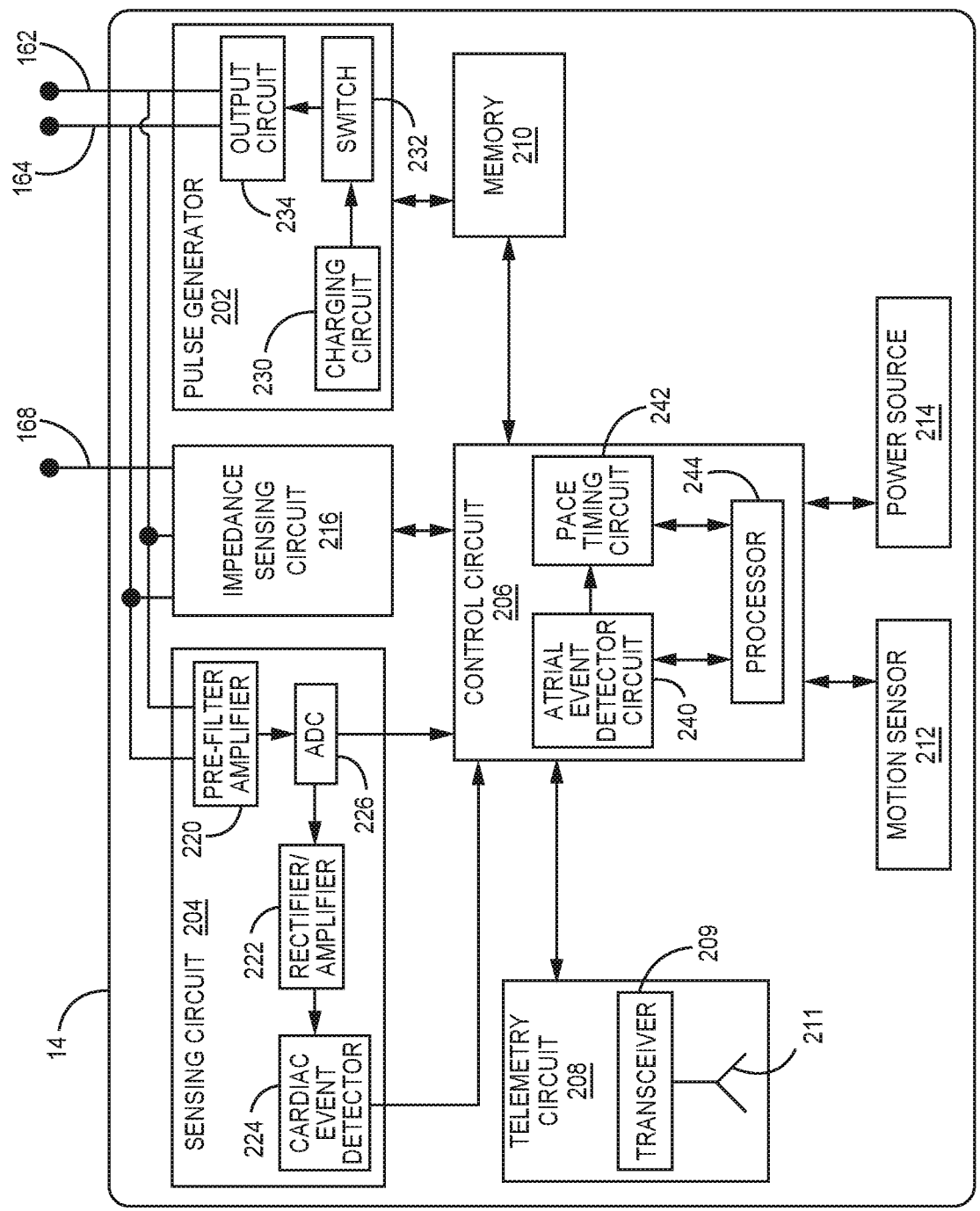
FIG. 3 is a schematic diagram of an example configuration of the pacemaker shown in FIG. 1.

FIG. 3 is a schematic diagram of an example configuration of pacemaker 14 shown in FIG. 1. Pacemaker 14 includes a pulse generator 202, a cardiac electrical signal sensing circuit 204, a control circuit 206, memory 210, telemetry circuit 208, motion sensor 212, power source 214 and impedance sensing circuit 216. The various circuits represented in FIG. 3 may be combined on one or more integrated circuit boards which may include a specific integrated circuit (ASIC), an electronic circuit, a processor (shared, dedicated, or group) and memory that execute one or more software or firmware programs, a combinational logic circuit, state machine or other suitable components that provide the described functionality.

Pulse generator 202 generates electrical pacing pulses that are delivered to the patient's heart via electrodes coupled to pacemaker 14, e.g., housing-based cathode electrode 164 and return anode electrode 162. Pulse generator 202 may include charging circuit 230, switching circuit 232 and an output circuit 234. Charging circuit 230 may include a holding capacitor that may be charged to a pacing pulse amplitude that is a multiple of the battery voltage signal of power source 214 under the control of a voltage regulator. The pacing pulse amplitude may be set based on a control signal from control circuit 206. Switching circuit 232 may control when the holding capacitor of charging circuit 230 is coupled to the output circuit 234 for delivering the pacing pulse. For example, switching circuit 232 may include a switch that is activated by a timing signal received from pace timing circuit 242 of control circuit 206 upon expiration of a pacing interval and kept closed for a programmed pacing pulse width to enable discharging of the holding capacitor of charging circuit 230. The holding capacitor, previously charged to the pacing pulse voltage amplitude, is discharged across electrodes 162 and 164 through the output capacitor of output circuit 234 for the programmed pacing pulse duration. Examples of pacing circuitry generally disclosed in U.S. Pat. No. 5,507,782 (Kieval, et al.) and in commonly assigned U.S. Pat. No. 8,532,785 (Crutchfield, et al.), both of which patents are incorporated herein by reference in their entirety, may be implemented in pacemaker 14 for charging a pacing capacitor to a predetermined pacing pulse amplitude under the control of control circuit 206 for generating and delivering a pacing pulse.

Cardiac electrical signal sensing circuit 204 is configured to sense a cardiac electrical signal via electrodes 162 and 164 and produce an intraventricular EGM signal. The cardiac electrical signal is received by a pre-filter and amplifier circuit 220. Pre-filter and amplifier circuit 220 may include a high pass filter to remove DC offset, e.g., a 2.5 to 5 Hz high pass filter, or a wideband filter having a passband of 2.5 Hz to 100 Hz to remove DC offset and high frequency noise. Pre-filter and amplifier circuit 220 may further include an amplifier to amplify the "raw" cardiac electrical signal passed to analog-to-digital converter (ADC) 226. The digital signal from ADC 226 may be passed to rectifier and amplifier circuit 222, which may include a rectifier, bandpass filter, and amplifier for passing the filtered and rectified cardiac electrical signal to cardiac event detector 224.

Cardiac event detector 224 may include a sense amplifier or other detection circuitry that compares the incoming rectified, cardiac electrical signal to an R-wave detection threshold, which may be an auto-adjusting threshold. When the incoming signal crosses the R-wave detection threshold, the cardiac event detector 224 produces an R-wave sensed event signal that is passed to control circuit 206. In other examples, cardiac event detector 224 may receive the digital output of ADC 226 for detecting R-waves by a comparator, morphological signal analysis of the digital EGM signal by a processor, or other R-wave detection techniques. R-wave sensed event signals passed from R-wave detector 224 to control circuit 206 may be used for scheduling or inhibiting ventricular pacing pulses, determining ventricular rate intervals, e.g., "RR intervals" (RRIs) between two consecutively received R-wave sensed event signals, and for use in identifying the timing of ventricular electrical events by atrial event detector circuit 240 for facilitating detection of atrial systolic events from a signal received from motion sensor 212 or impedance sensing circuit 216.

In some examples, cardiac event detector 224 may be configured to sense P-waves from the cardiac electrical signal received by electrodes 162 and 164. Cardiac event detector 224 may compare the incoming signal to a P-wave sensing threshold and produce a P-wave sensed event signal passed to control circuit 206 in response to a threshold crossing. When pacemaker 14 is configured to sense R-waves and P-waves, sensing circuit 204 may include two different sensing channels, each including filters, amplifiers, ADC, rectifier and cardiac event detector configured to amplify and filter cardiac electrical signals received via one or two different sensing electrode pairs (if available) for separately sensing R-waves and P-waves from the cardiac electrical signals. P-wave sensing may be used for verifying atrial events sensed from a motion sensor signal or impedance signal or vice versa. In some examples, P-wave sensed event signals are used by control circuit 206 for starting an AV interval for controlling atrial synchronous ventricular pacing pulses delivered by pulse generator 202.

Motion sensor 212 may be a single axis, one-dimensional sensor or a multi-axis sensor, e.g., a two-dimensional or three-dimensional sensor, with each axis providing a signal that may be analyzed individually or in combination. Motion sensor 212 produces an electrical signal correlated to motion or vibration of sensor 212 (and pacemaker 14), e.g., when subjected to flowing blood, cardiac motion and patient body motion due to physical activity such as exercise and activities of daily living or other motion imparted on the patient such as riding in a car. One example of an accelerometer for use in implantable medical devices is generally disclosed in U.S. Pat. No. 5,885,471 (Ruben, et al.), incorporated herein by reference in its entirety. An implantable medical device arrangement including a piezoelectric accelerometer for detecting patient motion is disclosed, for example, in U.S. Pat. No. 4,485,813 (Anderson, et al.) and U.S. Pat. No. 5,052,388 (Sivula, et al.), both of which patents are hereby incorporated by reference herein in their entirety. Examples of three-dimensional accelerometers that may be implemented in pacemaker 14 and used for detecting atrial systolic mechanical events in the techniques disclosed herein are generally described in U.S. Pat. No. 5,593,431 (Sheldon) and U.S. Pat. No. 6,044,297 (Sheldon), both of which are incorporated herein by reference in their entirety. Other accelerometer designs may be used for producing an electrical signal that is correlated to motion imparted on pacemaker 14 due to ventricular and atrial events and patient physical activity.

Each axis of a single or multi-dimensional accelerometer may be defined by a piezoelectric element, micro-electrical mechanical system (MEMS) device or other sensor element capable of producing an electrical signal in response to changes in acceleration imparted on the sensor element, e.g., by converting the acceleration to a force or displacement that is converted to the electrical signal. In a multi-dimensional accelerometer, the sensor elements may be arranged orthogonally with each sensor element axis orthogonal relative to the other sensor element axes. Orthogonal arrangement of the elements of a multi-axis accelerometer, however, is not necessarily required.

Motion sensor 212 may include filters, amplifiers, rectifiers, an analog-to-digital converter (ADC) and/or other components for producing an intraventricular motion signal passed to control circuit 206. For example, each vector signal corresponding to each individual axis of a multi-axis accelerometer may be filtered by a high pass filter, e.g., a 10 Hz high pass filter, and rectified for use by atrial event detector circuit 240 for sensing atrial systolic events, for example as described below in conjunction with FIGS. 4-6. The high pass filter may be lowered (e.g., to 5 Hz) if needed to detect atrial event signals that have lower frequency content. In some examples, high pass filtering is performed with no low pass filtering. In other examples, each accelerometer axis signal is filtered by a low pass filter, e.g., a 30 Hz low pass filter, with or without high pass filtering.

Motion sensor 212 may be used for sensing atrial systolic mechanical events for scheduling ventricular pacing pulses delivered by pulse generator 202 during atrial synchronous ventricular pacing. Additionally or alternatively, motion sensor 212 may provide a motion signal to control circuit 206 for determining a patient physical activity metric for providing rate responsive ventricular pacing that supports the patient's metabolic demand. Motion sensor 212 is implemented as an accelerometer in the examples described herein. Motion sensor 212 is not limited to being an accelerometer, however, and other motion sensors may be utilized in pacemaker 14 for producing an intraventricular motion signal for use in detecting cardiac motion signals and/or determining a patient physical activity metric. Examples of motion sensors that may be implemented in motion sensor 212 include piezoelectric sensors and MEMS devices.

Motion sensor 212 may include separate filtering of the accelerometer signal for passing a motion signal to control circuit 206 for use in detecting patient physical activity level. For example, 1 Hz high pass filtering of the raw accelerometer signal may produce a patient physical activity signal with DC components removed from which a patient physical activity metric may be determined. Control circuit 206 may be configured to determine a sensor indicated ventricular pacing rate (SIR) from the patient physical activity metric to control pulse generator 202 to deliver rate responsive ventricular pacing (asynchronous to atrial systolic events) at the SIR in order to meet the patient's metabolic demand during periods of increased physical activity.

Increased patient physical activity signals present in the motion signal produced by motion sensor 212 may reduce the reliability of atrial mechanical event sensing from the motion signal for use in controlling atrial synchronized ventricular pacing. As described below, control circuit 206 may control impedance sensing circuit 216 to produce an intraventricular impedance signal for use in confirming atrial event sensing from the motion signal during periods of increased patient physical activity or increased heart rate. In other examples, impedance sensing circuit 216 may be enabled by control circuit 206 to produce an impedance signal during periods of increased patient physical activity or increased heart rate so that atrial systolic events may be sensed directly from the impedance signal (which may include determining a derivative of the impedance signal) instead of detecting atrial systolic events from the motion signal until atrial event sensing from the intraventricular motion signal is deemed more reliable.

Impedance sensing circuit 216 includes a drive signal source for injecting an impedance drive signal via electrodes 162 and 164 (or electrode 168 in combination with either electrode 162 and 164). The drive signal source may be a sinusoidal current (or voltage) source and the resultant impedance signal may be a voltage (or current) signal that develops across the recording electrode pair. The resultant signal may be used directly as the impedance signal or converted to an actual impedance signal using the resultant signal developed across the recording electrode pair and the known drive signal. The drive signal may have a frequency between about 0.1 Hz to about 1 MHz, e.g., between 4 Hz to 100 KHz, and is delivered at an amplitude that is below that required to capture the heart to avoid inadvertently pacing or depolarizing the myocardium.

In one example, a raw impedance signal is received using electrodes 168 and electrode 162, both located along the peripheral sidewall 105 of pacemaker 14. Impedance sensing circuit 216 further includes one or more filters, amplifiers and ADC for producing an intraventricular impedance signal from the resultant raw signal that develops across a recording electrode pair selected from electrodes 162, 164 and 168. The intraventricular impedance signal may be a total impedance signal, a real impedance signal or an imaginary impedance signal. Impedance sensing circuit 216 may include one or more differentiators, such as an operational amplifier differentiator circuit, for producing the first and/or second derivatives of the impedance signal.

The impedance sensing circuit 216 may include a comparator or other threshold detector for comparing the intraventricular impedance signal to a threshold for use in detecting or confirming atrial systolic events. In other examples, impedance sensing circuit 216 produces a digital impedance signal that may be passed to control circuit 206 for use in detecting cardiac events. Atrial event detection based on an intraventricular impedance signal is described below in conjunction with FIG. 6 and the flow charts presented herein.

Control circuit 206 includes an atrial event detector circuit 240, pace timing circuit 242, and processor 244. Atrial event detector circuit 240 is configured to detect atrial mechanical events from an intraventricular motion signal received from motion sensor 212 and/or intraventricular impedance signal received from impedance sensing circuit 216. Control circuit 206 may receive R-wave sensed event signals, P-wave sensed event signals, and/or digital cardiac electrical signals from sensing circuit 204 for use in detecting and confirming cardiac events and controlling ventricular pacing. For example, R-wave sensed event signals may be passed to pace timing circuit 242 for inhibiting scheduled ventricular pacing pulses during atrial synchronous ventricular pacing or scheduling ventricular pacing pulses when pacemaker 14 is operating in a non-atrial tracking (asynchronous) ventricular pacing mode. An asynchronous ventricular pacing mode is an operating mode of pacemaker 14 during which control circuit 206 controls pulse generator 202 to deliver ventricular pacing pulses according to a ventricular pacing rate, e.g., a base or minimum lower pacing rate or a temporary lower rate. A temporary lower rate may be a pacing rate that is greater than the base pacing rate and is set according to a patient physical activity metric determined from the motion signal produced by motion sensor 212 in some examples. Examples of asynchronous ventricular pacing modes include VVI(R) and VDI(R) pacing modes. An atrial synchronous ventricular pacing mode is an operating mode of pacemaker 14 during which control circuit 206 senses atrial events, sets an AV pacing interval in response to each sensed atrial event, and delivers a ventricular pacing pulse upon expiration of the AV pacing interval such that ventricular pacing pulses are synchronized to the sensed atrial events by the AV pacing interval. An atrial synchronous ventricular pacing mode is sometimes referred to as a VDI pacing mode.

R-wave sensed event signals may be passed to atrial event detector circuit 240 for use in setting atrial blanking periods and/or time windows used by control circuit 206 in sensing atrial systolic events from the motion sensor signal and/or impedance signal. In some examples, atrial event detector circuit 240 receives a motion signal from motion sensor 212 and may start an atrial blanking period in response to a ventricular electrical event, e.g., an R-wave sensed event signal from sensing circuit 204 or delivery of a pacing pulse by pulse generator 202. The blanking period may correspond to a time period after the ventricular electrical event during which ventricular mechanical events corresponding to ventricular contraction, valve closure and isovolumic relaxation are expected to occur. Motion signal peaks that occur during the atrial blanking period are not sensed as atrial events to minimize the likelihood of falsely sensing a ventricular event signal as the atrial systolic event.

Atrial event detector circuit 240 may set time windows corresponding to the passive ventricular filling phase and the active ventricular filling phase of the cardiac cycle based on the timing of a preceding ventricular electrical event, either an R-wave sensed event signal or a ventricular pacing pulse. The earliest crossing of an atrial event sensing threshold by the motion sensor signal during these windows may be detected as the atrial systolic event. As described below, two different atrial event sensing threshold amplitude values may be established for applying to the motion signal during the passive filling phase window and after the passive filling phase window (during an active filling phase window).

In other examples, impedance sensing circuit 216 passes an intraventricular impedance signal to atrial event detector circuit 240. Atrial event detector circuit 240 may detect the timing of atrial mechanical systole from the impedance signal waveform and generate an atrial event detection signal in response to detecting the mechanical atrial systolic event. As described below in conjunction with FIG. 6, impedance sensing circuit 240 may produce a first derivative signal and/or a second derivative signal of the impedance signal received. The timing of mechanical atrial systole may be detected from the first or second derivative signal by atrial event detector circuit 240. Atrial events may be sensed directly from the impedance signal (or derivative thereof), or the impedance signal (or derivative thereof) may be used in setting a passive ventricular filling phase window and/or active ventricular filling phase window that are applied to the motion signal from motion sensor 212 for sensing atrial systolic events from the motion signal.

Atrial event detector circuit 240 passes an atrial event detection signal to processor 244 and/or pace timing circuit 242 in response to detecting an atrial systolic event. Processor 244 may include one or more clocks for generating clock signals that are used by pace timing circuit 242 to time out an AV pacing interval that is started upon receipt of an atrial event detection signal from atrial event detector circuit 240. Pace timing circuit 242 may include one or more pacing escape interval timers or counters that are used to time out pacing intervals, which may be programmable and stored in memory 210 and retrieved by processor 244. Other examples of atrial event sensing for use in controlling atrial synchronized ventricular pacing by an intracardiac ventricular pacemaker are generally disclosed in U.S. Pat. No. 9,399,140 (Cho, et al.) and U.S. Publication No. 2018/0161580 (Demmer, et al), both of which are incorporated herein by reference in their entirety.

Pace timing circuit 242 (or processor 244) may additionally receive R-wave sensed event signals from R-wave detector 224 for use in controlling the timing of pacing pulses delivered by pulse generator 202. Pace timing circuit 242 may include a lower pacing rate interval timer for controlling a lower ventricular pacing rate. For example, if an atrial systolic event is not detected before a lower pacing rate interval expires, a ventricular pacing pulse may be delivered by pulse generator 202 upon expiration of the lower pacing rate interval to prevent ventricular asystole and maintain a minimum ventricular rate. In order to avoid abrupt changes in ventricular rate, control circuit 206 may be configured to set the ventricular pacing rate interval to a rate smoothing interval. The rate smoothing interval may be determined based on one or more preceding ventricular event intervals. For example, a ventricular pacing pulse delivered in the absence of a sensed atrial event may be delivered at an interval that is set based on a preceding ventricular rate interval, e.g., a mean or median Vpace-to-Vpace interval or a mean or median RR interval. For example, a rate smoothing interval may be set to 100 to 150 ms greater than an actual ventricular rate interval determined from delivered ventricular pacing pulses and/or sensed R-waves.

Control circuit 206 may control pulse generator 202 to generate and deliver ventricular pacing pulses according to various pacing modes and control switching between the pacing modes. For instance, control circuit 206 may control pulse generator 202 to deliver atrial synchronous ventricular pacing pulses by sensing atrial systolic events, e.g., from the motion signal or the impedance signal, and setting an AV pacing interval. At other times, control circuit 206 may control pulse generator 202 to deliver ventricular pacing pulses in a non-atrial tracking or asynchronous ventricular pacing mode, e.g., VVI or VDI pacing mode. During periods of increased patient activity, control circuit 206 may control pulse generator 202 to deliver ventricular pacing pulses in a rate response, asynchronous ventricular pacing mode, e.g., VVIR or VDIR pacing mode.

Control circuit 206 may be configured to determine when to switch between asynchronous, synchronous and rate response pacing modes. For example, pacing mode switching criteria may be based on the rate of sensed atrial events, a patient physical activity metric determined from the motion signal, actual ventricular rate or other criteria relating to the patient's need for pacing and/or the reliability of atrial event sensing for delivering synchronous ventricular pacing. Examples of techniques for controlling pacing mode switching are given in the above-incorporated U.S. Pat. No. 9,399,140 (Cho, et al.) and in U.S. Publication No. 2018/0154154 (Sheldon, et al.), incorporated herein by reference in its entirety. In general, the pacing mode may be switched from an atrial synchronous pacing mode when atrial sensing is deemed unreliable or when a higher ventricular pacing rate is needed to support the patient's physical activity. The pacing mode may be switched from asynchronous pacing back to the atrial synchronous pacing mode when atrial event sensing is confirmed or when patient physical activity is decreased such that ventricular rate support is no longer needed.

Control circuit 206 may determine a patient activity metric from the motion signal received from motion sensor 212 at a desired frequency, e.g., every second, every 2 seconds, etc., for use in determining a sensor-indicated pacing rate (SIR). The activity metric may be determined as a count of amplitude threshold crossings by the motion signal or sample point amplitude summation or integration of the motion signal in various examples. The SIR may vary between a programmed minimum base rate during periods of rest (activity metric is less than or equal to a minimum resting activity threshold level) and a maximum upper pacing rate during periods of maximum exertion (activity metric is equal or greater than a maximum activity threshold level). The SIR may be determined according to an SIR transfer function defining a relationship between patient activity level and a target heart rate, which may include different rates of change of the SIR over different ranges of the activity metric. Examples of methods determining a SIR from an intraventricular motion signal are generally disclosed in U.S. Pat. No. 9,724,518 (Sheldon, et al.), incorporated herein by reference in its entirety. Any type of patient physical activity sensor that produces a signal that is correlated to metabolic demand may be used in controlling rate responsive ventricular pacing during an asynchronous pacing mode.

Processor 244 may retrieve programmable pacing control parameters from memory 210, such as pacing pulse amplitude and pacing pulse width, which are passed to pulse generator 202 for controlling pacing pulse delivery. In addition to providing control signals to pace timing circuit 242 and pulse generator 202 for controlling pacing pulse delivery, processor 244 may provide sensing control signals to cardiac electrical signal sensing circuit 204, impedance sensing circuit 216, motion sensor 212 and atrial event detector circuit 240 for sensing cardiac events, including sensing atrial events from the motion sensor signal and/or impedance signal as described below. Control signals may control sensing threshold amplitudes, sensing windows, blanking periods, refractory periods or the like. Memory 210 may include computer-readable instructions that, when executed by processor 244, cause control circuit 206 to perform various functions attributed throughout this disclosure to pacemaker 14. The computer-readable instructions may be encoded within memory 210. Memory 210 may include any non-transitory, computer-readable storage media including any volatile, non-volatile, magnetic, optical, or electrical media, such as a random access memory (RAM), read-only memory (ROM), non-volatile RAM (NVRAM), electrically-erasable programmable ROM (EEPROM), flash memory, or other digital media.

Power source 214 is enclosed in battery subassembly 160 shown in FIG. 2 and provides power to each of the other circuits and components of pacemaker 14 as required. Power source 214 may include one or more energy storage devices, such as one or more rechargeable or non-rechargeable batteries. The connections between power source 214 and other pacemaker circuits and components are not shown in FIG. 3 for the sake of clarity but are to be understood from the general block diagram of FIG. 3. For example power source 214 may provide power to charging circuit 230 for charging a holding capacitor to a pacing voltage amplitude, current to switch 232 and other circuitry included in pulse generator 202 as needed to generate and deliver pacing pulses. Impedance sensing circuit 216 receives power from power source 214 for generating a drive signal and for converting a resultant raw impedance signal to a digital intraventricular impedance waveform and/or digital derivative signal when impedance signal sensing is enabled. Power source 214 also provides power to telemetry circuit 208, motion sensor 212, and cardiac electrical signal sensing circuit 204 as well as memory 210 as needed.

Telemetry circuit 208 includes a transceiver 209 and antenna 211 for transferring and receiving data, e.g., via a radio frequency (RF) communication link. Telemetry circuit 208 may be capable of bi-directional communication with external device 20 (FIG. 1) as described above. Motion signals, impedance signals, cardiac electrical signals, and/or data derived therefrom may be transmitted by telemetry circuit 208 to external device 20. Programmable control parameters and programming commands for performing atrial event detection and ventricular pacing control according to the techniques disclosed herein may be received by telemetry circuit 208 and stored in memory 210 for access by control circuit 206.

The functions attributed to pacemaker 14 herein may be embodied as one or more processors, controllers, hardware, firmware, software, or any combination thereof. Depiction of different features as specific circuitry is intended to highlight different functional aspects and does not necessarily imply that such functions must be realized by separate hardware, firmware or software components or by any particular circuit architecture. Rather, functionality associated with one or more circuits described herein may be performed by separate hardware, firmware or software components, or integrated within common hardware, firmware or software components. For example, atrial systolic event detection from the motion sensor signal and/or impedance signal and ventricular pacing control operations performed by pacemaker 14 may be implemented in control circuit 206 executing instructions stored in memory 210 and relying on input from sensing circuit 204 and motion sensor 212.

The operation of circuitry included in pacemaker 14 as disclosed herein should not be construed as reflective of a specific form of hardware, firmware and software necessary to practice the techniques described. It is believed that the particular form of software, hardware and/or firmware will be determined primarily by the particular system architecture employed in the pacemaker 14 and by the particular sensing and therapy delivery circuitry employed by the pacemaker 14. Providing software, hardware, and/or firmware to accomplish the described functionality in the context of any modern pacemaker, given the disclosure herein, is within the abilities of one of skill in the art.

Figure 4:
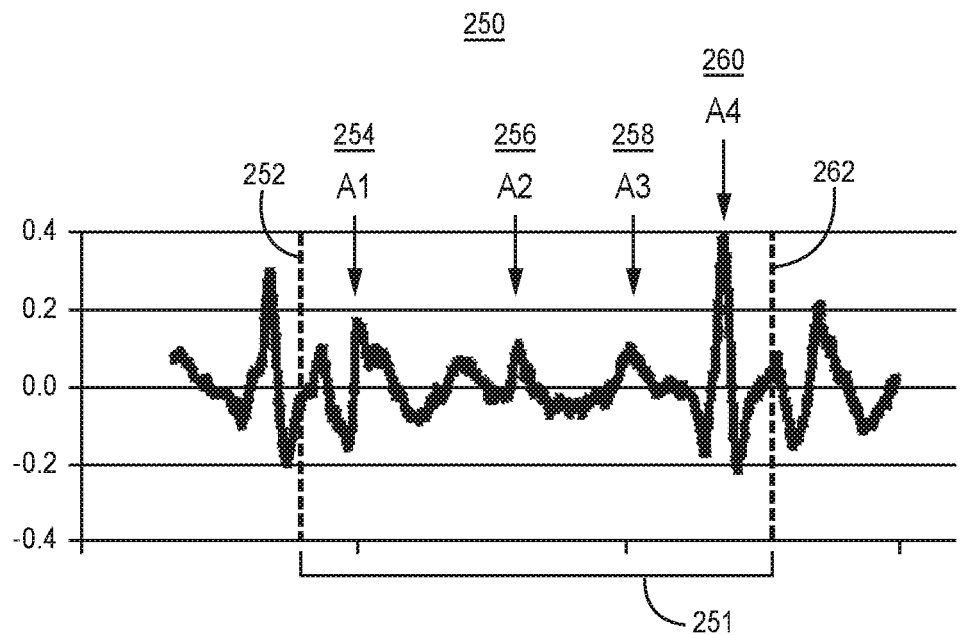
FIG. 4 is an example of a motion sensor signal that may be produced by a motion sensor included in the pacemaker of FIG. 1.

FIG. 4 is an example of a motion sensor signal 250 that may be produced by motion sensor 212 over a cardiac cycle. Vertical dashed lines 252 and 262 denote the timing of two consecutive ventricular events (an intrinsic ventricular depolarization or a ventricular pace), marking the respective beginning and end of the ventricular cycle 251. The motion signal includes an A1 event 254, an A2 event 256, an A3 event 258 and an A4 event 260. The A1 event 254 is an acceleration signal (in this example when motion sensor 212 includes an accelerometer) that occurs during ventricular contraction and marks the approximate onset of ventricular mechanical systole. The A1 event is also referred to herein as a "ventricular contraction event." The A2 event 256 is an acceleration signal that may occur during closure of the aortic and pulmonic valves and marks the approximate offset or end of ventricular mechanical systole. The A2 event may also mark the beginning of ventricular diastole and is generally an indication of the isovolumic relaxation phase of the ventricles that occurs with aortic and pulmonic valve closure. The A3 event 258 is an acceleration signal that occurs during passive ventricular filling and marks ventricular mechanical diastole. The A3 event is also referred to herein as the "ventricular passive filling event."

The A4 event 260 is an acceleration signal that occurs during atrial contraction and active ventricular filling and marks atrial mechanical systole. The A4 event 260 may also be referred to herein as the "atrial systolic event" or merely the "atrial event," and is the atrial systolic event that is detected from motion sensor signal 250 by atrial event detector circuit 240. The A4 event 260 may be sensed during an atrial synchronous ventricular pacing mode, for example, for controlling pace timing circuit 242 to trigger ventricular pacing pulse delivery by starting an AV pacing interval in response to detecting the A4 event 260. In some examples, control circuit 206 may be configured to detect one or more of the A1, A2, and A3 events from motion sensor signal 250, for at least some ventricular cardiac cycles, for use in positively detecting the A4 event 260 and setting atrial event detection control parameters. The A1, A2 and/or A3 events may be detected and characterized to avoid false detection of A4 events and promote reliable A4 event detection for proper timing of atrial-synchronized ventricular pacing pulses.

Figure 5:
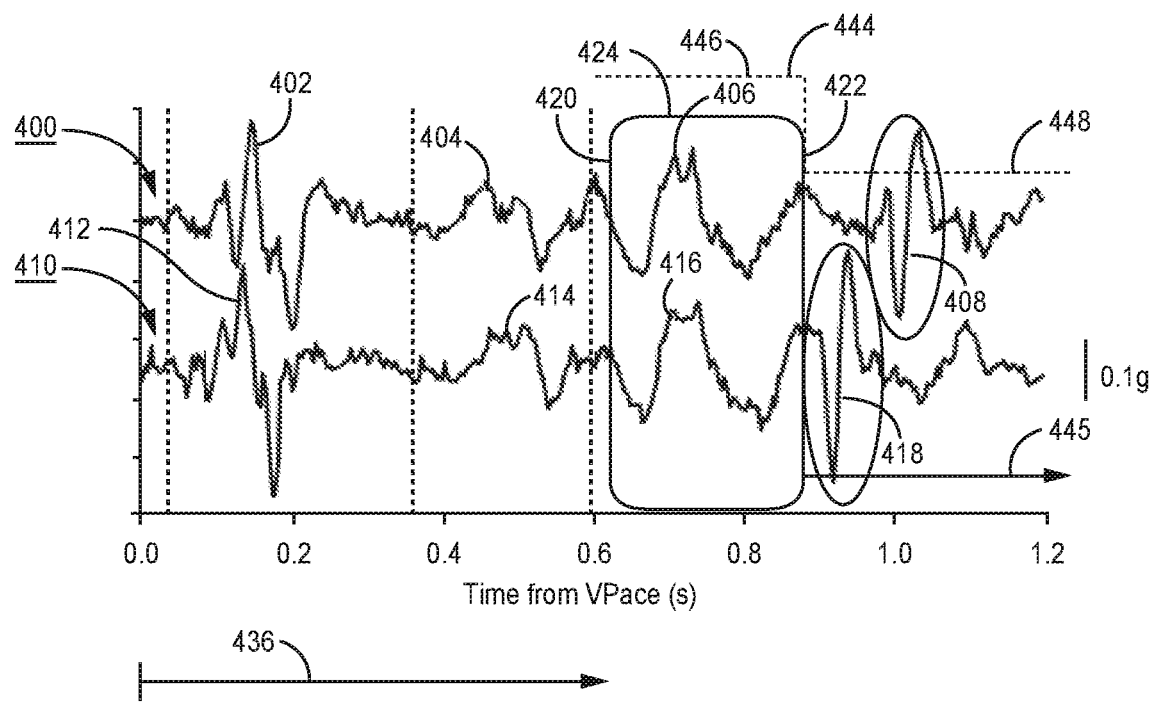
FIG. 5 depicts example motion sensor signals that may be produced by the pacemaker of FIG. 1 over two different cardiac cycles.

FIG. 5 depicts example motion sensor signals 400 and 410 acquired over two different cardiac cycles. A ventricular pacing pulse is delivered at time 0.0 seconds for both cardiac cycles. The top sensor signal 400 is received over one cardiac cycle and the bottom sensor signal 401 is received over a different cardiac cycle. The two signals 400 and 410 are aligned in time at 0.0 seconds, the time of the ventricular pacing pulse delivery. While motion signals 400 and 410 and motion signal 250 of FIG. 4 are shown as raw accelerometer signals, it is recognized that motion sensor 212 may produce a filtered, amplified and rectified signal that is passed to control circuit 206 for detecting atrial events by atrial event detector circuit 240.

The A1 events 402 and 412 of the respective motion sensor signals 400 and 410, which occur during ventricular contraction, are observed to be well-aligned in time following the ventricular pacing pulse at time 0.0 seconds. Similarly, the A2 events 404 and 414 and the A3 events 406 and 416 (occurring during passive ventricular filling) are well-aligned in time. Since the A1, A2 and A3 events are ventricular events, occurring during ventricular contraction, ventricular isovolumic relaxation, and passive ventricular filling, respectively, these events are expected to occur at relatively consistent intervals following a ventricular electrical event, the ventricular pacing pulse in this example, and relative to each other. The time relationship of the A1, A2 and A3 events may be different following a ventricular pacing pulse compared to following a sensed intrinsic R-wave; however, during a stable paced or intrinsic ventricular rhythm, the relative timing of A1, A2 and A3 events to each other and the immediately preceding ventricular electrical event is expected to be consistent.

The A4 events 408 and 418 of the first and second motion sensor signals 400 and 410 respectively are not aligned in time. The A4 event occurs due to atrial systole and as such the time interval to the A4 event following the immediately preceding ventricular electrical event (sensed R-wave or ventricular pacing pulse) and the preceding A1 through A3 events may vary between cardiac cycles as the atrial rate changes.

The consistency of the timing of the A1 through A3 events relative to each other and the immediately preceding ventricular electrical event may be used for determining an atrial blanking period 436 and increasing confidence in reliably detecting A4 events 408 and 418. The atrial systolic event is not detected during the atrial blanking period 436 which may extend from the ventricular electrical event (at time 0.0) to an estimated onset of ventricular diastole, for example. An A3 sensing window 424 may be set having a starting time 420 corresponding to the end of the atrial blanking period 436 and an ending time 422. The atrial blanking interval 436 may be 600 ms, as an example, and the A3 window 424 may extend 200 ms after the atrial blanking interval 436.

A4 events 408 and 418 may be detected based on a multi-level A4 detection threshold 444. As seen by the lower motion sensor signal 410, the A4 event 418 may occur earlier after the A3 window 424 due to changes in atrial rate. In some instances, as the atrial rate increases, the A4 event 418 may occur within the A3 window 424. When this occurs, the A3 event 416 and the A4 event 418 may fuse as passive and active ventricular filling occur together. The fused A3/A4 event may have a high amplitude, even greater than the amplitude of either the A3 event 416 or the A4 event 418 when they occur separately. As such, in some examples the A4 detection threshold 444 includes a first, higher A4 threshold amplitude 446 established for detecting an early A4 event that is fused with the A3 event during the A3 window 424. A second, lower A4 threshold amplitude 448 may be established for detecting relatively later A4 events, after the ending time 422 of the A3 window 424. An A4 window 445 may extend from the end of the A3 window 424 until an atrial event is sensed or a ventricular event occurs, whichever occurs first. The earliest crossing of the A4 detection threshold 444 by the motion sensor signal after the starting time 420 of the A3 window (or after the expiration of the atrial blanking period 436) may be sensed as the atrial systolic event. Various examples of an intracardiac pacemaker configured to detect atrial systolic events from a motion sensor signal for delivering atrial synchronous ventricular pacing are disclosed in commonly-assigned U.S. Publication No. 2018/0085589 (Splett et al.), U.S. Publication No. 2018/0085588 (Sheldon, et al.), U.S. Publication No. 2018/0117337 (Demmer, et al.), U.S. Publication No. 2018/0154154 (Sheldon, et al.), and U.S. Publication No. 2018/0161580 (Demmer, et al.), all of which are incorporated herein by reference in their entirety. The techniques disclosed herein for using an intraventricular impedance signal in atrial event sensing may be implemented in combination with any of the examples presented in the foregoing incorporated references.

Figure 6:
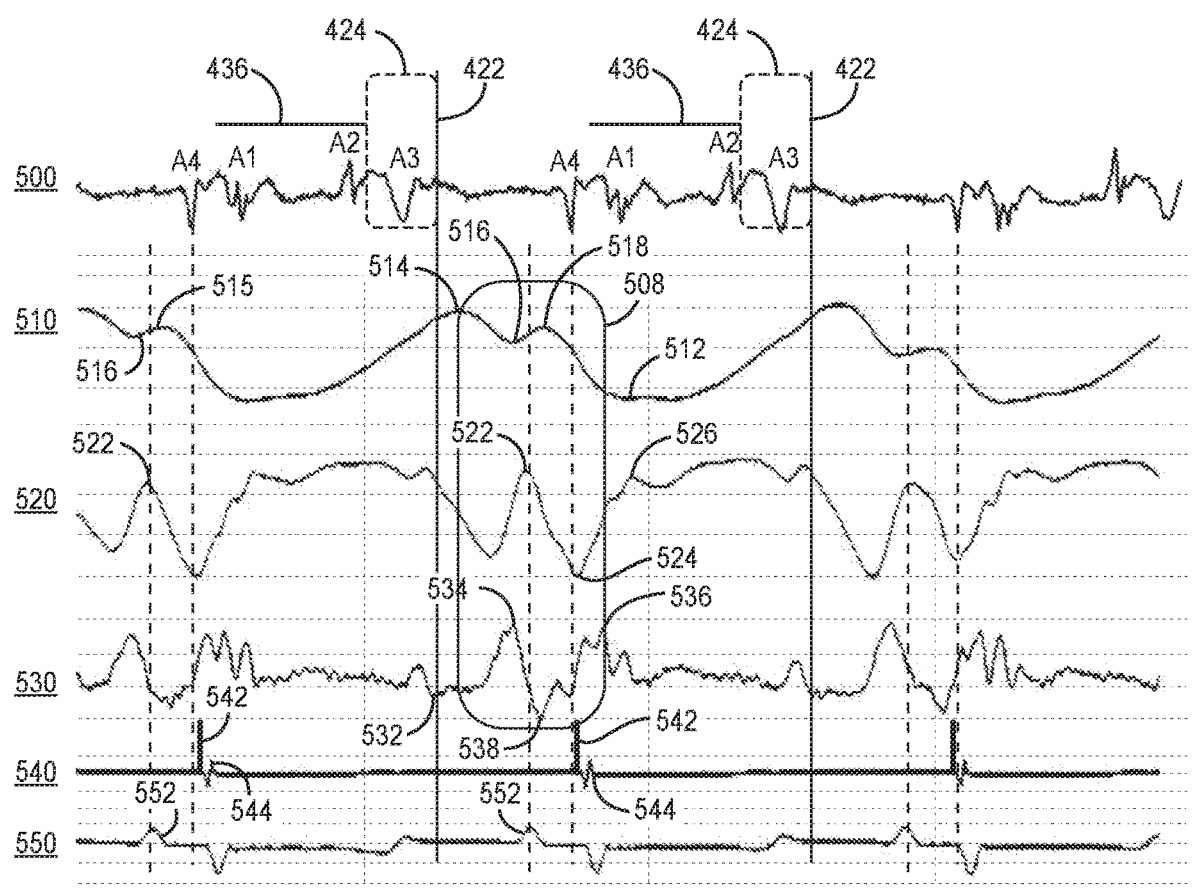
FIG. 6 depicts an intraventricular motion signal, an intraventricular impedance signal, and a ventricular electrogram (EGM) signal that may be produced by the pacemaker of FIG. 1 and an electrocardiogram (ECG) signal.

FIG. 6 depicts a motion signal 500 that may be produced by motion sensor 212, an impedance signal 510 that may be produced by impedance sensing circuit 216, a ventricular electrogram (EGM) signal 540 that may be produced by cardiac electrical signal sensing circuit 204, and an electrocardiogram (ECG) signal 550. Ventricular pacing pulse markers 542 are shown along EGM signal 540 followed by evoked R-wave signals 544. A first derivative signal 520 and a second derivative signal 530 may be produced from the impedance signal 510 by impedance sensing circuit 216 and passed to control circuit 206 for use in atrial event detection. The relative timing of features of the intraventricular impedance signal 510, shown as a total impedance signal, motion signal 500, EGM 540 and ECG 550 illustrates techniques disclosed herein for using impedance signal 510 in detecting atrial systolic events from an intraventricular signal. Detecting atrial systolic events using impedance signal 510 may include detecting the atrial systolic event directly from impedance signal 510 (which may include determining first derivative signal 520 and/or second derivative signal 530), using the impedance signal 510 for confirming atrial systolic events sensed from motion signal 500, and/or establishing A4 event sensing parameters used by atrial event detector circuit 240 for sensing atrial systolic events from motion signal 500.

The A1, A2, A3 and A4 event signals are denoted along motion signal 500. While motion signal 500 and other signals depicted in FIG. 6 are shown as non-rectified signals, it is recognized that any of the signals may be rectified and passed to control circuit 206 for cardiac event detection. Control circuit 206 may start an atrial blanking period 436 in response to a ventricular pacing pulse 542 being delivered. Atrial events are not sensed during atrial blanking period 436 to avoid oversensing of the ventricular events (e.g., A1 and A2 signals) as atrial events. When atrial events are being sensed from the motion signal 500, control circuit 206 may set an A3 window 424 having an ending time 422. As described above in conjunction with FIG. 5, a higher A4 sensing threshold amplitude may be applied during the A3 window 424, and a lower A4 sensing threshold amplitude may be applied after the A3 window ending time 422 until an A4 event is sensed (or the next ventricular electrical event occurs).

In some examples, atrial event detector circuit 240 may receive impedance signal 510, the impedance first derivative signal 520 and/or second derivative signal 530 from impedance sensing circuit 216 for detecting the atrial mechanical systolic event. As seen in FIG. 6, the A4 events of motion signal 500, which are attendant to the active ventricular filling phase or "atrial kick," correspond in time to a minimum peak 524 of the impedance first derivative signal 520. Accordingly, the atrial mechanical systolic event may be detected by atrial event detector circuit 240 by detecting a minimum negative peak 524 of the first derivative signal 520 (or a maximum negative slope of impedance signal 510) in one example. Control circuit 206 may be configured to detect the atrial systolic mechanical events by detecting one or more features of the impedance signal 510, first derivative signal 520, or second derivative signal 530 for triggering ventricular pacing pulses 542 in an atrial synchronous ventricular pacing mode.

In some examples, an atrial event sensing window 508 may be established by producing an impedance signal 510 and detecting one or more features of impedance signal 510 (or a derivative thereof) that are correlated in time to the ventricular diastolic period and atrial systole. In one example, the starting time of atrial event sensing window 508 may be established by producing impedance signal 510 and detecting maximum peak 514. The starting time may be set at the maximum peak 514 or at an offset earlier or later than the maximum peak 514. The ending time of window 508 may be based on a fixed time interval, identifying a subsequent minimum peak 512, identifying maximum peak 526 of first derivative signal 520, or identifying maximum peak 536 of second derivative signal 530, as examples.

Window 508 may be established based on the impedance signal 510 during a set-up process in which impedance signal 510 is produced throughout the cardiac cycle or following blanking period 436. For example the starting and ending times of window 508 may be determined from the impedance signal 510 (or derivative thereof) relative to a ventricular electrical event, such as pacing pulse 542 or R-wave 544. After establishing (or updating) window 508, the impedance signal may be produced only during the atrial sensing window 508 on a beat-by-beat basis for sensing atrial events. In some examples the starting time of window 508 is determined so that atrial event detection circuit 240 starts searching for impedance signal features at the starting time of window 508 but the ending time may be undefined. Atrial event detection circuit 240 may search for inflection 516 or maximum peak 518 of impedance signal 510, maximum peak 522 (corresponding to positive slope 515 after inflection point 516), minimum peak 524 of the first derivative signal 520, minimum peak 538 of second derivative signal 530, or other selected feature or combination of features of impedance signal 510, first derivative signal 520, and/or second derivative signal 530 during the atrial event sensing window 508 for detecting the timing of the atrial event.

It is recognized that depending on the orientation of the recording electrodes used to receive the raw impedance signal and/or implant orientation of pacemaker 14 the peaks and valleys of the raw impedance signal may be reversed from the intraventricular impedance signal shown in FIG. 6. In some examples, the intraventricular impedance signal produced by impedance sensing circuit 216 may be a rectified or inverted signal. Atrial events may be sensed from the impedance signal 510 (or derivative thereof) on a beat by beat basis for triggering atrial synchronized ventricular pacing pulses delivered upon expiration of an AV interval set in response to sensing the atrial event from the impedance signal.

A triggered ventricular pacing pulse may be scheduled at an AV interval following an identified feature of the impedance signal 510, first derivative signal 520, or second derivative signal 530 that promotes completion of active ventricular filling prior to ventricular contraction induced by the ventricular pacing pulse. For instance, when the minimum peak 524 of first derivative signal 520 is detected as the atrial event, a ventricular pacing pulse 542 may be triggered to occur with a upon expiration of a relatively short AV pacing interval, e.g., 10 ms. When an earlier feature of the impedance signal 510 or a derivative thereof is identified, e.g., inflection point 516 of impedance signal 510, maximum peak 522 of first derivative signal 520, or maximum peak 534 of second derivative signal 530 is detected as an indication of the timing of the atrial systolic event, the AV pacing interval may be set to a longer interval, e.g., 50 to 200 ms, to provide optimized atrial synchronized ventricular pacing.

In other examples, detecting atrial events using the intraventricular impedance signal includes verifying A4 event sensing from motion signal 500. Detection of one or more features from the impedance signal 510, first derivative signal 520 or second derivative signal 530 may be used for verifying A4 event sensing from the motion signal 500. The P-wave 552 (of ECG signal 550), which is attendant to the electrical depolarization of the atria, is observed to correspond in time with the maximum positive peak 522 of the first derivative signal 520. Detection of inflection point 516 or maximum peak 522 following inflection point 516, both of which precede the A4 event of motion signal 500, may be performed by atrial event detector circuit 240 for confirming a subsequently detected A4 event from motion signal 500. If the A4 event is not sensed within an expected time interval of an identified feature of the impedance signal 510, first derivative signal 520 or second derivative signal 530, A4 event sensing is not confirmed or may be deemed unreliable.

In some instances, the motion signal 500 may be used by pacemaker 14 for sensing atrial events during an atrial synchronous ventricular pacing mode. On a periodic basis, or if undersensing or oversensing of A4 events is suspected, control circuit 206 may control impedance sensing circuit 216 to produce impedance signal 510, first derivative signal 520 and/or second derivative signal 530 for use by atrial event detector circuit 240 for verifying the relative timing of a feature of the impedance signal relative to an A4 sensed event. For instance, if the A4 event is sensed within a threshold time range of the minimum peak 524 of first derivative signal 520, control circuit 206 may confirm A4 event sensing. The threshold time range may be a predetermined value, e.g., within 20 ms before or after the minimum peak 524. In other examples the threshold time range may be established based on the impedance signal 510 or second derivative signal 530. For example, the A4 events may be required to be sensed within a time interval range extending from the first maximum peak 534 to the second maximum peak 536 of the second derivative signal 530.

If an A4 event is sensed outside a threshold time range of a feature of impedance signal 510 (which may be determined from a first or second derivative signal 520 or 530), the event sensed as an A4 event may be a ventricular A3 or A1 event or other non-cardiac motion signal due to patient activity or other motion signal noise. The sensed event is not confirmed as an A4 event. Parameters used to control A4 event sensing, such as the A3 window 424 and A4 sensing threshold 444 (shown in FIG. 5), may be adjusted by control circuit 206 and/or other corrective action may be taken, such as switching to an asynchronous ventricular pacing mode or remaining in the atrial synchronous ventricular pacing mode but enabling atrial event sensing directly from the intraventricular impedance signal until A4 sensing can be confirmed.

In other examples, the intraventricular impedance signal 510 is used in detecting atrial systolic events by identifying one or more features of the impedance signal 510 (or a derivative thereof) during a process for establishing A4 sensing control parameters. For instance, the ending time 422 of A3 window 424 may be set based on a feature of impedance signal 510, such as the time of the maximum peak 514 of impedance signal 510 or the earliest minimum peak 532 of the second derivative signal 530 that occurs after atrial blanking period 436. During an initial set up process or when A4 sensing is not confirmed, control circuit 206 may update the A3 window ending time 422 based on a feature identified from the impedance signal 510. In other examples, during an initial set up process or when atrial event sensing from the motion signal is not confirmed, the A4 sensing threshold amplitude 446 (FIG. 5) applied during the A3 window 424 and the second lower sensing threshold amplitude 448 (FIG. 5) after the A3 window 424 may be updated or adjusted until A4 event sensing is confirmed based on relative timing of correlated features of the impedance signal 510. Adjustment of the A4 sensing threshold amplitude may restore A4 event sensing within a threshold time interval or range of an identified feature of the impedance signal 510, thereby confirming A4 event sensing.

Figure 7:
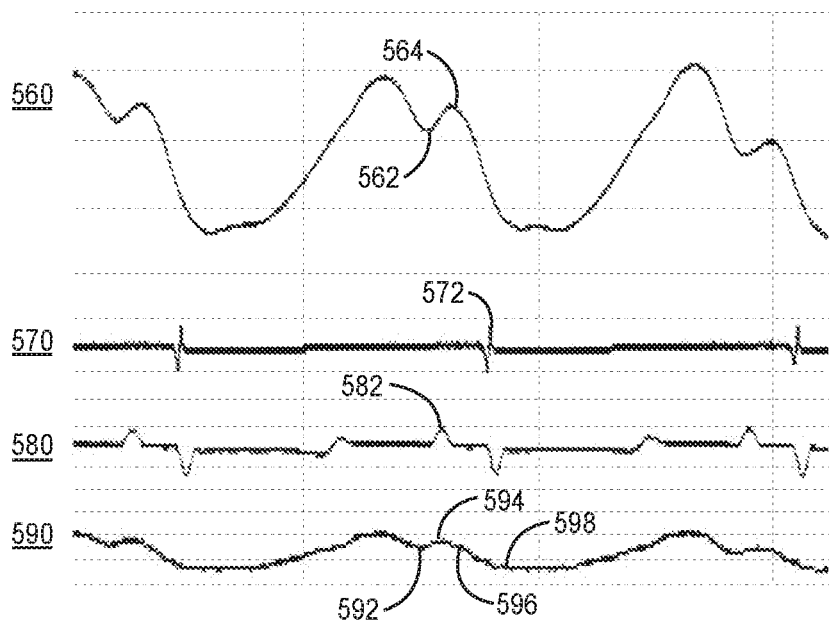
FIG. 7 depicts the magnitude waveform and the phase angle waveform of an intraventricular impedance signal that may be produced by the pacemaker of FIG. 1.

FIG. 7 depicts the magnitude waveform 560 and the phase waveform 590 of an intraventricular impedance signal that may be produced by impedance sensing circuit 216. A corresponding ventricular electrogram signal 570 and ECG signal 580 are also shown to indicate the relative timing of R-waves 572 that may be sensed by cardiac electrical signal sensing circuit 204 and P-waves 582 that may be observed on the ECG signal 580. As can be observed in FIG. 7, features of the impedance phase waveform 590 correspond in time to analogous features of the impedance magnitude waveform 560. For example, an inflection point 562 of the magnitude waveform and an inflection point 592 of the phase waveform both occur just prior to P-wave 582. P-wave 582 is immediately followed by a local maximum peak 564 of the magnitude waveform 560 and a local maximum peak 594 of the phase angle waveform 590.

Accordingly, a feature of the phase waveform 590 of the complex impedance signal resulting from a sinusoidal drive signal may be used in atrial event sensing as a surrogate for, or in any combination with, features of the magnitude waveform 560 and/or total impedance signal features described above in conjunction with FIG. 6. As examples, the inflection point 592, the local maximum peak 594, the peak negative slope 596, or minimum 598 or any combination thereof, of the complex impedance phase waveform may be detected by control circuit 206 for use in atrial event sensing according to any of the methods disclosed herein. As such, the "intraventricular impedance signal" produced by impedance sensing circuit 216 and used in atrial systolic event sensing may be the magnitude and/or phase of a total impedance signal.

Figure 8:
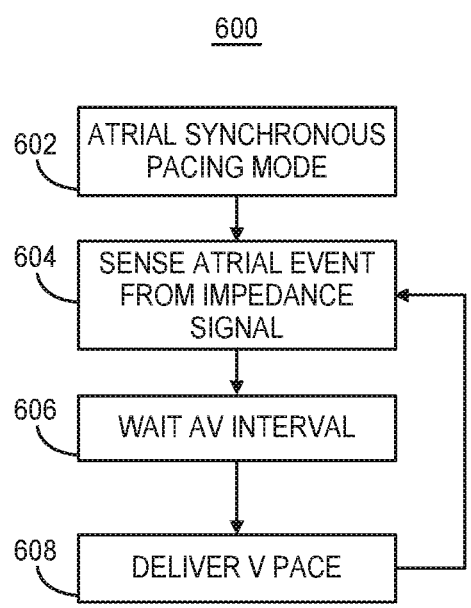
FIG. 8 is a flow chart of one method of ventricular pacing that may be performed by the pacemaker of FIG.1.

FIG. 8 is a flow chart 600 of one method of ventricular pacing that may be performed by pacemaker 14. At block 602, control circuit 206 is programmed to operate in an atrial synchronous ventricular pacing mode. Control circuit 206 enables impedance sensing circuit 216 to produce an impedance signal that is passed to atrial event detector circuit 240 for sensing atrial events. The atrial systolic mechanical event may be sensed at block 604 using the impedance signal 510, first derivative signal 520 or second derivative signal 530 (all shown in FIG. 6) by detecting one or more features of the respective signal that correspond in time to the A4 event of motion signal 500. In one example, control circuit 206 detects a decreasing impedance signal indicative of ventricular filling. In response to detecting a decreasing impedance signal, e.g., following maximum peak 514 (FIG. 6), control circuit 206 searches for a rising or maximum positive peak of the first or second derivative signals 520 or 530 or a minimum peak 524 or 538 of the first or second derivative signals 520 or 530, respectively. The maximum or minimum peak of the first or second derivative signal may be detected as the atrial systolic event that corresponds in time to the A4 event signal of the motion signal and atrial mechanical contraction.

In some examples, sensing an atrial event at block 604 may include enabling impedance sensing circuit during an atrial event sensing window, e.g., window 508 shown in FIG. 6. By enabling impedance sensing circuit 216 to produce an impedance drive signal during an atrial event sensing window 508, power required to produce the intraventricular impedance signal may be conserved compared to producing an impedance signal throughout the cardiac cycle. Atrial event detector circuit 240 may search for one or more features of the impedance signal 510, first derivative signal 520 or second derivative signal 530 (FIG. 6) for sensing the atrial event from the impedance signal produced by impedance sensing circuit 216 during atrial event sensing window 508.

At block 606, pace timing circuit 242 starts an AV pacing interval in response to atrial event detector circuit 240 detecting the atrial systolic event from the impedance signal. The AV interval may be set to an appropriate interval that promotes ventricular pacing pulse delivery synchronized to the sensed atrial event such that the onset of ventricular contraction is synchronized to the end of the A4 or atrial kick event without impeding ventricular filling. The AV pacing interval may be set to 10 ms to 200 ms, as examples, depending on the timing of the detected impedance signal feature relative to the A4 event of the motion signal. Upon expiration of the AV interval, pulse generator 202 is configured to deliver a ventricular pacing pulse at block 608. While not shown explicitly in FIG. 8, it is to be understood that if an intrinsic R-wave is sensed during the AV interval by cardiac electrical signal sensing circuit 204, the scheduled ventricular pacing pulse may be withheld. Ventricular pacing pulses are triggered by a sensed atrial event and inhibited by a sensed R-wave during the atrial synchronous ventricular pacing mode. Control circuit 206 starts an atrial blanking period in response to a sensed R-wave or delivered ventricular pacing pulse and waits for the next sensed atrial event at block 604.

Figure 9:
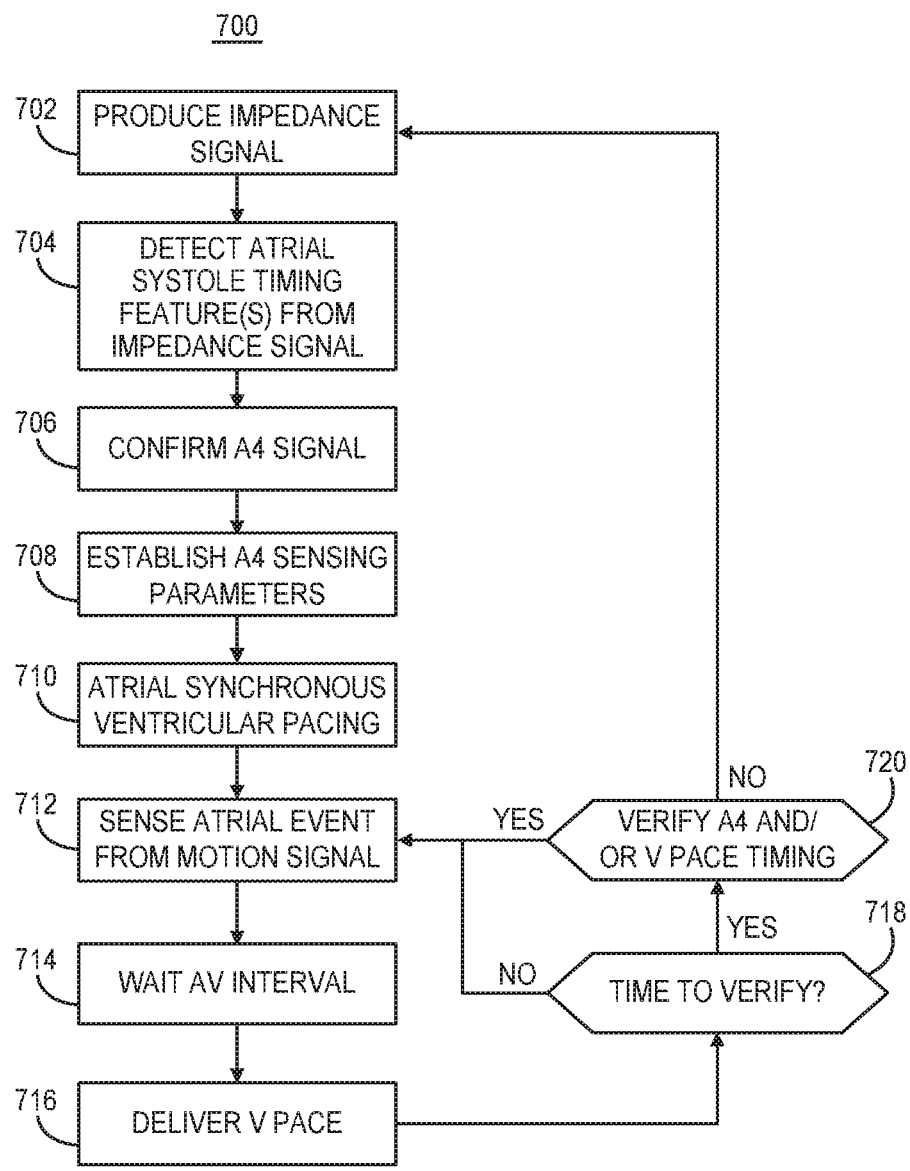
FIG. 9 is a flow chart of a method performed by the pacemaker of FIG. 1 for establishing atrial event signal sensing parameters using an impedance signal and for controlling atrial synchronized ventricular pacing according to another example.

FIG. 9 is a flow chart 700 of a method performed by pacemaker 14 for establishing A4 sensing parameters using an impedance signal and for controlling atrial synchronized ventricular pacing according to another example. At block 702, control circuit 206 enables the impedance sensing circuit 216 to produce an impedance signal. Impedance sensing circuit 216 may be powered by power source 214 to generate a drive signal and produce the resultant impedance signal at time intervals controlled by control circuit 206. For example, control circuit 206 may control impedance sensing circuit 216 to produce an impedance signal for one or more consecutive or non-consecutive ventricular cycles or for one or more consecutive or non-consecutive pre-determined time intervals. For instance, control circuit 206 may enable impedance sensing circuit 216 to produce an impedance signal for multiple ventricular cycles based on the timing of R-wave sensed event signals received from cardiac electrical signal sensing circuit 204 or based on the timing of delivered ventricular pacing pulses.

The process for establishing A4 sensing parameters, e.g., as represented by blocks 702 through 708, may be performed when AV conduction is intact, during episodes of R-wave sensing by sensing circuit 204. The process may be performed when the heart rate is below a threshold rate and is stable in some examples. At other times, the process for establishing A4 sensing parameters may be performed when the patient is experiencing AV block and ventricular pacing is required. Control circuit 206 may control pulse generator 202 to deliver atrial synchronized ventricular pacing based on sensing atrial mechanical systole from the impedance signal as described above in conjunction with FIG. 8.

The impedance signal produced at block 702 may be a voltage or current signal developed across a recording pair of electrodes selected from electrodes 162, 164 and 168 that is filtered, amplified and may be rectified in some examples. The impedance signal produced at block 702 may include determining a derivative of the impedance signal, such as the first and/or second derivative signal as shown in FIG. 6.

At block 704, control circuit 206 receives the impedance signal produced at block 702, and a processor 244 included in control circuit 206 may detect one or more atrial systole timing features from the impedance signal or a derivative thereof. With reference to FIG. 6, a maximum peak 518 of the impedance signal 510, a maximum peak 522 of the first derivative signal 520, a minimum peak 538 of the second derivative signal 530 or other feature of the impedance signal may be detected following a ventricular electrical event or following the maximum peak impedance 514 (corresponding to the end of ventricular systole) as an indication of the approximate onset of atrial systole. If AV conduction is intact, control circuit 206 may detect the atrial systole timing features from the impedance signal after each R-wave sensed event signal during one or more ventricular cycles.

If the patient is experiencing AV block, control circuit 206 may control pulse generator 202 to deliver ventricular pacing pulses following detection of an atrial systolic event feature of the impedance signal or a derivative thereof. In one example, when A4 sensing parameters are being established, ventricular pacing pulses may be triggered by detecting the minimum peak 512 of impedance signal 510 (corresponding to the end of ventricular diastole and maximum filling of the ventricles). Following delivery of each ventricular pacing pulse, the control circuit 206 may search for the maximum peak 514 of impedance signal 510, minimum peak 532 of the second derivative signal 530 or another feature that is correlated to the end of ventricular systole and the onset of atrial systole. An atrial blanking period may be applied following the ventricular pacing pulse to enable searching for the impedance signal features after ventricular systole.

At block 706, control circuit 206 may optionally confirm A4 event sensing from the motion signal during an expected time window relative to the one or more impedance signal features determined at block 704. For example, control circuit 206 may detect the minimum peak 524 of the first derivative signal 520. Control circuit 206 may confirm that an A4 event is sensed from motion signal 500 within an expected time interval range of the minimum peak 524 of the first derivative signal 520. At block 706, one or more A4 sensing parameters may be set based on a time interval determined from the ventricular electrical event (R-wave sensed event signal or ventricular pacing pulse) to a feature of the impedance signal. The time interval may be an average or median time interval determined over multiple ventricular cycles.

To illustrate, the time interval from a ventricular pacing pulse triggered in response to the minimum impedance 512 until the following maximum peak impedance 514 may be determined for each one of three to twelve ventricular cycles (or other predetermined number of ventricular cycles). A median time interval may be determined to represent the time from the start of ventricular systole until the end of ventricular systole. The median time interval may be used to establish the A3 window ending time 422 at block 708. The median time interval may be used directly as the A3 window ending time 422, or the median plus or minus an offset interval may be set as the A3 window ending time. Other example features of the impedance signal that may be used in establishing the A3 window are described above in conjunction with FIG. 6.

In examples that include confirming the A4 signal (block 706) relative to one or more features identified from the impedance signal, the peak amplitude of the confirmed A4 signal may be determined and used in establishing an A4 sensing threshold amplitude at block 708. In this way, the impedance signal produced by impedance sensing circuit 216 is used by control circuit 206 for establishing atrial event sensing parameters that are used for sensing the atrial systolic event from the motion signal produced by motion sensor 212. Other examples of establishing A4 event signal sensing parameters using the impedance signal are described above in conjunction with FIG. 6.

At block 710, control circuit 206 enables atrial synchronous ventricular pacing (if not already enabled) using the motion signal for sensing atrial events, e.g., in a VDD pacing mode using A4 event sensing. In some instances, control circuit 206 may already be operating in an atrial synchronous ventricular pacing mode but using the impedance signal for detecting atrial mechanical systolic events, e.g., as described in conjunction with FIG. 8. This situation may occur if the patient is experiencing AV block during the process for establishing the A4 sensing parameters.

If the A4 sensing parameters are established during ventricular sensing, when AV conduction is intact, control circuit 206 may be operating in an asynchronous ventricular pacing mode, e.g., VVI(R) or VDI(R) mode, with a base ventricular pacing rate set to a relatively low rate, e.g., 40 to 50 pulses per minute or less, to allow AV conduction to occur but avoid ventricular asystole. Control circuit 206 may switch from an asynchronous ventricular pacing mode to an atrial synchronous pacing mode at block 710 in response to AV block being detected. AV block may be detected based on a predetermined number of ventricular pacing pulses being delivered at the base pacing rate in one example.

At block 712, A4 signals are sensed by control circuit 206 from the motion signal received from motion sensor 212 using the A4 sensing parameter(s) established at block 708. In one example, at least an A3 window ending time established based on the impedance signal is used during A4 sensing from the motion signal. The A4 sensing threshold, which may include a first, higher amplitude during the A3 window and a second, lower amplitude after the A3 window ending time, is applied to the motion signal. The earliest crossing of the A4 sensing threshold by the motion signal is detected as the A4 event. In response to detecting the A4 event, at block 712, an AV pacing interval is started at block 714. Upon expiration of the AV interval, pulse generator 202 delivers a ventricular pacing pulse at block 716.

The process of flow chart 700 may be repeated to update A4 sensing parameters periodically. In some examples, if A4 undersensing or oversensing is suspected, the process of FIG. 9 is repeated to re-establish A4 sensing parameters. In other examples, each time control circuit 206 switches to an atrial synchronous ventricular pacing mode, e.g., in response to a user programming command or detection of AV block or other switching condition, the process of FIG. 9 may be performed to establish or update the A4 sensing parameter(s).

In some examples, control circuit 206 may verify A4 sensing and/or appropriate timing of the ventricular pacing pulse during the atrial synchronous ventricular pacing mode. Verification may be performed beat-by-beat by enabling impedance sensing circuit 216 to produce an impedance signal, at least during a selected time window during the cardiac cycle, for verifying the A4 event sensed from the motion signal based on a feature of the impedance signal and/or verifying appropriate timing of the ventricular pacing pulse relative to a minimum impedance corresponding to maximum ventricular filling. In order to conserve power source 214, verification of A4 sensing and/or ventricular pacing pulse timing may be performed periodically or triggered in response to a condition that may indicate a change in A4 sensing reliability. For example, control circuit 206 may set a timer upon enabling atrial synchronous ventricular pacing based on A4 event sensing at block 710. Control circuit 206 may determine that it is time to verify A4 event sensing and/or appropriate ventricular pacing timing at block 718 in response to the timer expiring. Verification may be performed once per minute, once per hour, once per day or other selected frequency.

In other examples, a condition that may be indicative of a change in A4 signal timing, A4 signal amplitude, the presence or timing of other signals present in the motion signal such as patient physical activity signals, or other condition that warrants A4 sensing verification may trigger the verification. For example, control circuit 206 may be configured to detect a change in heart rate (e.g., based on A4-A4 intervals or Vpace-Vpace intervals), a change in the A3-A4 interval, or a change in patient physical activity at block 718 for triggering a verification at block 720. If a triggering event or expiration of a predetermined verification time interval has not occurred, control circuit 206 returns to block 712 to continue sensing A4 events and controlling atrial synchronized ventricular pacing.

When control circuit 206 determines that it is time to verify A4 event sensing and/or ventricular pace timing (block 718), control circuit 206 enables impedance sensing circuit 216 at block 720 to produce an impedance signal, which may be continuous or only during a predetermined time window corresponding to ventricular diastole and atrial systole. A4 event sensing may be verified using any of the methods described above based on relative timing of a sensed A4 event from a feature of the impedance signal. In other examples, verification of appropriate ventricular pacing pulse timing may be based on determining that the ventricular pacing pulse occurs within a threshold time of a minimum impedance 512, a corresponding positive-going peak 526 of the first derivative signal 520 or maximum peak 536 of the second derivative signal 530.

In some examples, the ventricular pacing pulse may be delayed, e.g., by temporarily extending the AV interval on one or more cardiac cycles, to verify that that a ventricular pacing pulse scheduled to occur at the programmed AV interval following an A4 sensed event would occur at or near the minimum peak 524 of the first derivative signal. If, at block 720, the scheduled ventricular pacing pulse delivery time is found to be much earlier or later in the impedance signal 510 based on an A4 sensed event time and the programmed AV interval and/or if the A4 event is found to be sensed outside a threshold range of a reference feature of the impedance signal 510 or derivative thereof, appropriate A4 and/or ventricular pacing timing is not verified at block 720. Control circuit 206 may return to block 702 for re-establishing the A4 sensing parameters. In this way, the impedance signal may be used intermittently during atrial synchronized ventricular pacing utilizing A4 sensing from the motion signal to verify A4 sensing and appropriate timing of ventricular pacing pulse delivery that does not impair ventricular filling.

Figure 10:
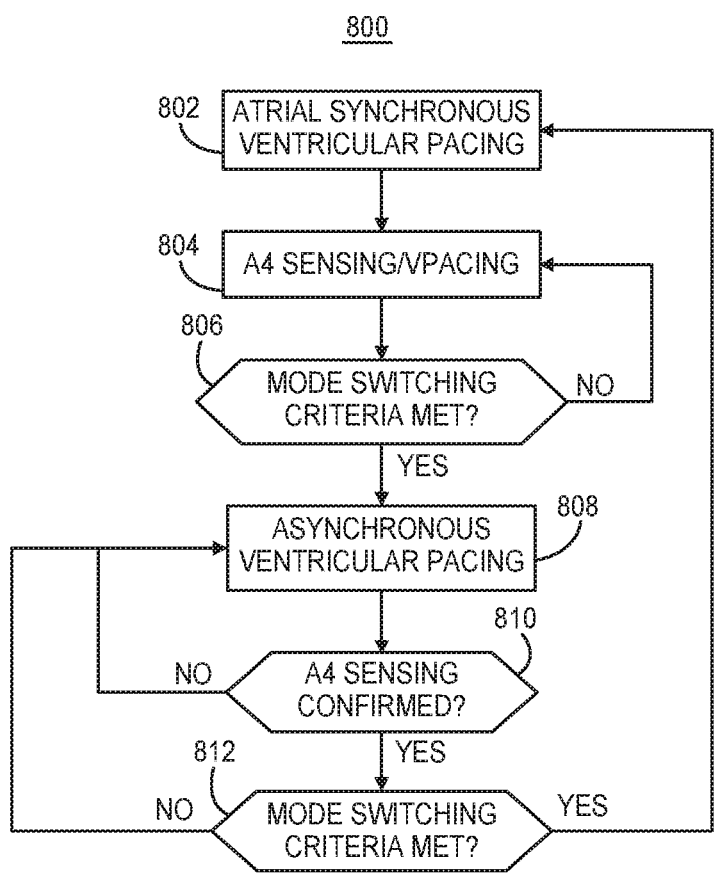
FIG. 10 is a flow chart of a method performed by the pacemaker of FIG. 1 for controlling atrial synchronized ventricular pacing according to another example.

FIG. 10 is a flow chart 800 of a method performed by pacemaker 14 for controlling atrial synchronized ventricular pacing according to another example. At block 802, pacemaker 14 operates in an atrial synchronous ventricular pacing mode. As indicated at block 804, this pacing mode includes sensing A4 events from the motion signal and delivering a ventricular pacing pulse at an AV pacing interval following each sensed A4 event.

At block 806, control circuit 206 determines that pacing mode switching criteria are met. Pacing mode switching criteria may be met by one or more monitored parameters indicative of reduced reliability of A4 event sensing, which may include A4 event oversensing and/or A4 event undersensing. Examples of techniques for controlling pacing mode switching are given in the above-incorporated U.S. Pat. No. 9,399,140 (Cho, et al.) and in U.S. Publication No. 2018/0154154 (Sheldon, et al.), incorporated herein by reference in its entirety. As examples, control circuit 206 may determine that pacing mode switching criteria are met in response to a sensed atrial rate exceeding a threshold, an actual ventricular rate exceeding a threshold, a threshold number of cardiac cycles with no A4 sensed events, a patient activity metric exceeding a threshold, or any combination thereof.

In other examples, mode switching criteria are met at block 806 in response to failing to verify A4 event sensing from the motion signal based on the impedance signal using any of the techniques described above in conjunction with FIG. 6. During the atrial synchronous ventricular pacing mode, control circuit 206 may periodically enable the impedance sensing circuit 216 to produce an impedance signal for verifying A4 event sensing based on the timing of a sensed A4 event relative to a feature determined from the impedance signal that corresponds to atrial systole. If the A4 event is not sensed from the motion signal within a threshold interval from a feature of the impedance signal, A4 event sensing is not confirmed and mode switching criteria may be met at block 806. If A4 event sensing is confirmed, control circuit 206 continues sensing A4 events and delivering synchronized ventricular pacing pulses (block 804).

Upon pacing mode switching criteria being met, control circuit 206 switches to an asynchronous ventricular pacing mode at block 808. During the asynchronous ventricular pacing mode, control circuit 206 controls pulse generator 202 to deliver ventricular pacing pulses according to a programmed lower ventricular pacing rate or according to a patient activity-based pacing rate, e.g., in a rate responsive pacing mode during which a target heart rate is determined from a patient activity metric determined from the motion signal.

During the asynchronous ventricular pacing mode, A4 event sensing and impedance signal generation may be enabled continuously or intermittently for determining if A4 sensing is confirmed based on impedance signal features. For example, at block 810, control circuit 206 may enable impedance sensing circuit 216 to produce an impedance signal and compare the relative timing of sensed A4 events to one or more features of the impedance signal or a derivative thereof. If A4 sensing is confirmed based on the expected timing of the sensed A4 event relative to an impedance signal feature, control circuit 206 may switch back to atrial synchronous ventricular pacing at block 802, with ventricular pacing pulses synchronized to sensed A4 events.

In the example shown, control circuit 206 may not switch back immediately after confirming A4 sensing, but may wait until other pacing mode switching criteria are met at block 812. For example, switching back to the atrial synchronous ventricular pacing mode may require that the patient physical activity and/or actual ventricular rate be less than a respective threshold in addition to A4 sensing being confirmed. In other examples, when A4 sensing is confirmed at block 810 based on an analysis of the impedance signal and the sensed A4 event timing, control circuit 206 may be configured to immediately switch back to the atrial synchronous ventricular pacing mode without waiting for other pacing mode switching criteria to become satisfied. As long as A4 sensing is deemed reliable, ventricular pacing pulses may be synchronized to the sensed A4 events.

In other examples, control circuit 206 may start the process of confirming A4 sensing at block 810 in response to determining that other mode switching criteria met at block 806 are no longer being met during the asynchronous ventricular pacing mode. For example, if an increased heart rate or increased patient physical activity caused the control circuit 206 to switch to asynchronous ventricular pacing, control circuit 206 may wait for the condition to reverse, e.g., the heart rate to decrease and/or the patient physical activity to decrease below a respective threshold rate or level, before checking if A4 sensing is confirmed at block 810.

The process of confirming A4 sensing during asynchronous ventricular pacing may require extending a ventricular pacing interval or withholding one ventricular pacing pulse to reduce the likelihood of the asynchronous ventricular contraction interfering with the detection of the atrial systolic event. When A4 event sensing is confirmed based on analysis of the impedance signal, control circuit 206 switches back to the atrial synchronous ventricular pacing mode using A4 event sensing at block 802.

Figure 11:
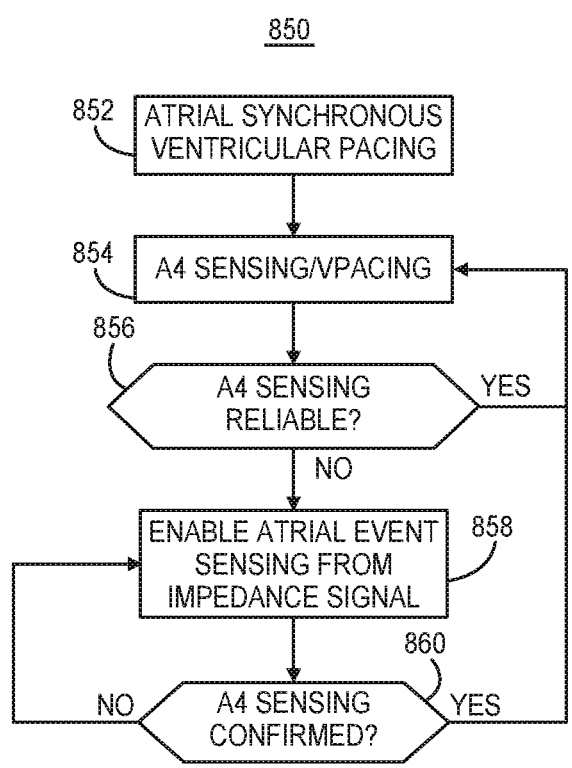
FIG. 11 is a flow chart of a method performed by the pacemaker of FIG. 1 for controlling ventricular pacing according to yet another example.

FIG. 11 is a flow chart 850 of a method performed by pacemaker 14 for controlling ventricular pacing according to another example. Control circuit 206 operates in an atrial synchronous ventricular pacing mode at block 852 by sensing A4 events from the motion signal and controlling pulse generator 202 to deliver ventricular pacing pulses synchronized to the sensed A4 events as indicated at block 854. The ventricular pacing pulses may be delivered at a programmed base or lower rate VV pacing interval in the absence of a sensed A4 event. In some examples, a ventricular pacing pulse is delivered at a rate smoothing interval when the rate smoothing interval expires without a sensed A4 event. The rate smoothing interval may be determined by control circuit 206 based on the actual ventricular rate, e.g., a median RR interval determined out of a predetermined number of preceding RR intervals (which may include paced and intrinsic ventricular beats).

At block 856, control circuit 206 may determine that A4 event sensing is, or is likely to become, unreliable. Unreliable A4 event sensing is determined when A4 events are either undersensed (sensed intermittently or not sensed at all) or oversensed (other cardiac or non-cardiac motion signals are falsely sensed as the A4 event signal) for one or more cardiac cycles. While a single undersensed or oversensed A4 event may not reach a threshold of unreliability, A4 under- or oversensing for multiple cardiac cycles may result in unacceptable variation or irregularity in the ventricular rate.

One or more conditions may be monitored for detecting or predicting unreliable A4 sensing at block 856. A4 undersensing may be detected by control circuit 206 when a threshold number of ventricular pacing pulses are delivered at a ventricular pacing interval, e.g., a rate smoothing interval, without sensing the A4 event. The ventricular pacing pulses delivered without an A4 sensed event may be consecutive or non-consecutive pacing pulses. For instance, three consecutive ventricular pacing pulses delivered without a sensed A4 event may be detected as unreliable A4 sensing at block 856 because undersensing may be suspected.

A4 oversensing may be suspected when the ventricular rate is increased above a threshold rate. In other examples, therefore, unreliable A4 sensing may be suspected or predicted if the patient physical activity metric exceeds a predetermined threshold or when the A3-A4 time interval shortens (indicating an increased atrial rate) or the A4 event is sensed during the A3 window. Various criteria may be defined for detecting or predicting an increased likelihood of A4 under- or oversensing for use in determining unreliable A4 sensing at block 856.

If A4 sensing is determined to be unreliable at block 856, control circuit 206 enables atrial event sensing from the impedance signal at block 858. Control circuit 206 enables impedance sensing circuit 216 to produce an impedance signal. Atrial event detector circuit 240 detects the timing of the atrial event from the impedance signal or a derivative thereof, e.g., according to any of the examples described above in conjunction with FIG. 6. Control circuit 206 continues to operate in the atrial synchronous ventricular pacing mode by detecting the atrial systolic event from the impedance signal and setting an AV pacing interval in response to detecting the atrial systolic event. The AV pacing interval may be different than the AV pacing interval used during A4 sensing for atrial synchronous ventricular pacing.

While continuing atrial synchronous ventricular pacing based on atrial event sensing from the impedance signal, control circuit 206 may confirm A4 event sensing based on the relative timing of one or more detected features of the impedance signal (or a derivative thereof) and a sensed A4 event. If A4 event sensing is not confirmed, e.g., based on the A4 event being sensed greater than a threshold time interval from an impedance signal feature, atrial synchronized ventricular pacing with atrial event sensing from the impedance signal may continue until A4 sensing is confirmed. Once confirmed, control circuit 206 may return to block 854 to disable impedance sensing circuit 216 to conserve power and to switch back to A4 sensing from the motion signal for triggering ventricular pacing pulses. In this way, pacemaker 14 may remain in the atrial synchronous ventricular pacing mode, even during times that A4 sensing may be unreliable, by switching to the impedance signal for atrial event sensing when A4 sensing from the motion signal is determined to be unreliable.

It should be understood that, depending on the example, certain acts or events of any of the methods described herein can be performed in a different sequence, may be added, merged, or left out altogether (e.g., not all described acts or events are necessary for the practice of the method). Moreover, in certain examples, acts or events may be performed concurrently, e.g., through multi-threaded processing, interrupt processing, or multiple processors, rather than sequentially. In addition, while certain aspects of this disclosure are described as being performed by a single circuit or unit for purposes of clarity, it should be understood that the techniques of this disclosure may be performed by a combination of units or circuits associated with, for example, a medical device.

In one or more examples, the functions described may be implemented in hardware, software, firmware, or any combination thereof. If implemented in software, the functions may be stored as one or more instructions or code on a computer-readable medium and executed by a hardware-based processing unit. Computer-readable media may include computer-readable storage media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor," as used herein may refer to any of the foregoing structure or any other structure suitable for implementation of the techniques described herein. Also, the techniques could be fully implemented in one or more circuits or logic elements.

Thus, a medical device has been presented in the foregoing description with reference to specific examples. It is to be understood that various aspects disclosed herein may be combined in different combinations than the specific combinations presented in the accompanying drawings. It is appreciated that various modifications to the referenced examples may be made without departing from the scope of the disclosure and the following claims.

What is claimed is:

1. A method performed by an intracardiac ventricular pacemaker, the method comprising:
producing an intraventricular impedance signal by an impedance sensing circuit;
producing a motion signal by a motion sensor;
detecting an atrial systolic event by a control circuit of the pacemaker using the intraventricular impedance signal by:
sensing an atrial event signal from the motion signal;
detecting at least one feature of a derivative of the intraventricular impedance signal corresponding to atrial systole;
determining that the atrial event signal sensed from the motion signal and the feature of the derivative of the intraventricular impedance signal are within a threshold time interval of each other; and
detecting the atrial systolic event in response to the atrial event signal sensed from the motion signal and the feature of the derivative of the intraventricular impedance signal being within a threshold time interval of each other;
in response to detecting the atrial systolic event, operating in an atrial synchronous ventricular pacing mode comprising:
sensing subsequent atrial event signals from the motion signal; and
delivering atrial synchronized ventricular pacing pulses, wherein each of the atrial synchronized ventricular pacing pulses is delivered at an atrioventricular pacing interval from a respective one of the subsequent atrial event signals sensed from the motion signal;
detecting at least one of an increased patient physical activity based on the motion signal or an increased heart rate based on the delivered atrial synchronized ventricular pacing pulses;
enabling the impedance sensing circuit to produce the intraventricular impedance signal in response to detecting at least one of the increased patient physical activity based on the motion signal or the increased heart rate based on the delivered atrial synchronized ventricular pacing pulses; and
switching from sensing the subsequent atrial event signals from the motion signal to sensing the subsequent atrial event signals from the impedance signal for controlling delivery of the atrial synchronized ventricular pacing pulses during the atrial synchronous ventricular pacing mode.

2. The method of claim 1, further comprising:
setting an ending time of a passive ventricular filling window based on the at least one feature of the intraventricular impedance signal;
setting an atrial event sensing threshold comprising a first threshold amplitude before the ending time of the passive ventricular filling window and a second threshold amplitude less than the first threshold amplitude after the passive ventricular filling window;
detecting the atrial systolic event from the motion signal during at least one subsequent ventricular cycle in response to an earliest crossing of the atrial event sensing threshold by the motion signal;
setting the atrioventricular pacing interval in response to detecting the atrial systolic event from the motion signal; and
delivering a ventricular pacing pulse upon expiration of the atrioventricular pacing interval.

3. The method of claim 1, wherein detecting the at least one feature of the intraventricular impedance signal comprises detecting at least one of:
a maximum peak of a first derivative signal of the intraventricular impedance signal;
a minimum peak of the first derivative signal of the intraventricular impedance signal;
a maximum peak of a second derivative signal of the intraventricular impedance signal; and
a minimum peak of the second derivative signal of the intraventricular impedance signal.

4. The method of claim 1, further comprising:
determining that the atrial event signal is not sensed from the motion signal during at least one subsequent ventricular cycle; and
switching to an asynchronous ventricular pacing mode for controlling the pulse generator to deliver ventricular pacing pulses according to a ventricular pacing rate in response to determining that the event signal is not sensed from the motion signal during the at least one subsequent ventricular cycle; and
delivering the ventricular pacing pulses according to the ventricular pacing rate during the asynchronous ventricular pacing mode.

5. The method of claim 1, further comprising:
switching from an atrial synchronous ventricular pacing mode to an asynchronous ventricular pacing mode;
delivering ventricular pacing pulses according to a ventricular pacing rate in response to switching to the asynchronous ventricular pacing mode;
confirming detection of the atrial systolic event using the intraventricular impedance signal during the asynchronous ventricular pacing mode; and
switching back to the atrial synchronous ventricular pacing mode in response to confirming the detection of the atrial systolic event.

6. The method of claim 1, further comprising:
receiving a raw impedance signal from a recording electrode pair comprising two electrodes on a lateral sidewall of a pacemaker housing that encloses the pulse generator, the impedance sensing circuit, and the control circuit and comprises a proximal end, a distal end and the lateral sidewall extending from the proximal end to the distal end; and
producing the intraventricular impedance signal from the raw impedance signal.

7. A non-transitory, computer-readable storage medium comprising a set of instructions which, when executed by a control circuit of an intracardiac ventricular pacemaker, cause the pacemaker to:
- produce an intraventricular impedance signal;
- producing a motion signal by a motion sensor;
- detect an atrial systolic event using the intraventricular impedance signal by:
  - sensing an atrial event signal from the motion signal;
  - detecting at least one feature of a derivative of the intraventricular impedance signal corresponding to atrial systole;
  - determining that the atrial event signal sensed from the motion signal and the feature of the derivative of the intraventricular impedance signal are within a threshold time interval of each other; and
  - detecting the atrial systolic event in response to the atrial event signal sensed from the motion signal and the feature of the derivative of the intraventricular impedance signal being within a threshold time interval of each other;
- in response to detecting the atrial systolic event, operate in an atrial synchronous ventricular pacing mode comprising:
  - sensing subsequent atrial event signals from the motion signal; and
  - delivering atrial synchronized ventricular pacing pulse wherein each of the atrial synchronized ventricular pacing pulses is delivered at an atrioventricular pacing interval from a respective one of the subsequent atrial event signals sensed from the motion signal;
- detect at least one of an increased patient physical activity based on the motion signal or an increased heart rate based on the delivered atrial synchronized ventricular pacing pulses;
- enable the impedance sensing circuit to produce the intraventricular impedance signal in response to detecting at least one of the increased patient physical activity or the increased heart rate; and
- switch from sensing the subsequent atrial event signals from the motion signal to sensing the subsequent atrial event signals from the impedance signal for controlling delivery of the atrial synchronized ventricular pacing pulses during the atrial synchronous ventricular pacing mode.

8. An intracardiac ventricular pacemaker comprising:
- an impedance sensing circuit configured to produce an intraventricular impedance signal;
- a motion sensor configured to produce a motion signal;
- a pulse generator configured to deliver a ventricular pacing pulse upon expiration of an atrioventricular pacing interval; and
- a control circuit in communication with the impedance sensing circuit, the motion sensor and the pulse generator, the control circuit configured to:
  - detect an atrial systolic event using the intraventricular impedance signal by:
    - sensing an atrial event signal from the motion signal;
    - detecting at least one feature of a derivative of the intraventricular impedance signal corresponding to atrial systole;
    - determining that the atrial event signal sensed from the motion signal and the feature of the derivative of the intraventricular impedance signal are within a threshold time interval of each other; and
    - detecting the atrial systolic event in response to the atrial event signal sensed from the motion signal and the feature of the derivative of the intraventricular impedance signal being within the threshold time interval of each other;
  - in response to detecting the atrial systolic event, operate in an atrial synchronous ventricular pacing mode comprising:
    - sensing subsequent atrial event signals from the motion signal;
    - controlling the pulse generator to deliver an atrial synchronized ventricular pacing pulse at the atrioventricular pacing interval from each of the subsequent sensed atrial event signals;
    - detecting at least one of an increased patient physical activity based on the motion signal or an increased heart rate based on the delivered atrial synchronized ventricular pacing pulses;
    - determining that the subsequent atrial event signal sensing from the motion signal is unreliable in response to detecting at least one of the increased patient physical activity or the increased heart rate;
    - enabling the impedance sensing circuit to produce the intraventricular impedance signal in response to determining that the subsequent atrial event signal sensing from the motion signal is unreliable; and
    - switching from sensing the subsequent atrial event signals from the motion signal to sensing subsequent atrial event signals from the impedance signal for controlling the pulse generator to deliver the atrial synchronized ventricular pacing pulses.

9. The pacemaker of claim 8, wherein:
the control circuit is further configured:
- set an ending time of a passive ventricular filling window based on the at least one feature of the intraventricular impedance signal;
- set an atrial event sensing threshold comprising a first threshold amplitude before the ending time of the passive ventricular filling window and a second threshold amplitude less than the first threshold amplitude after the passive ventricular filling window; and
- detect the atrial systolic event from the motion signal during at least one subsequent ventricular cycle in response to an earliest crossing of the atrial event sensing threshold by the motion signal; and
- set the atrioventricular pacing interval in response to detecting the atrial systolic event from the motion signal; and the pulse generator is configured to deliver a ventricular pacing pulse upon expiration of the atrioventricular pacing interval.

10. The pacemaker of claim 8, wherein the control circuit is configured to detect the at least one feature of the derivative of the intraventricular impedance signal by detecting at least one of:
- a maximum peak of a first derivative signal of the intraventricular impedance signal;
- a minimum peak of the first derivative signal of the intraventricular impedance signal;
- a maximum peak of a second derivative signal of the intraventricular impedance signal; and
- a minimum peak of the second derivative signal of the intraventricular impedance signal.

11. The pacemaker of claim 8, wherein:

the control circuit is further configured to:
- determine that the atrial event signal is not sensed from the motion signal during at least one subsequent ventricular cycle; and
- switch to an asynchronous ventricular pacing mode for controlling the pulse generator to deliver ventricular pacing pulses according to a ventricular pacing rate in response to determining that the atrial event signal is not sensed during the at least one subsequent ventricular cycle; and the pulse generator is configured to deliver the ventricular pacing pulses according to the ventricular pacing rate in response to the control circuit switching to the asynchronous ventricular pacing mode.

12. The pacemaker of claim 8, wherein:

the control circuit is further configured to switch from an atrial synchronous ventricular pacing mode to an asynchronous ventricular pacing mode;

the pulse generator is configured to deliver ventricular pacing pulses according to a ventricular pacing rate in response to the control circuit switching to the asynchronous ventricular pacing mode; and the control circuit is further configured to:
- confirm detecting of the atrial systolic event using the intraventricular impedance signal during the asynchronous ventricular pacing mode; and
- switch back to the atrial synchronous ventricular pacing mode in response to confirming the detecting of the atrial systolic event.

13. The pacemaker of claim 8, further comprising:

a pacemaker housing enclosing the pulse generator, the impedance sensing circuit, and the control circuit, the pacemaker housing comprising a proximal end, a distal end and a lateral sidewall extending from the proximal end to the distal end; and two electrodes on the lateral sidewall defining an impedance recording electrode pair coupled to the impedance sensing circuit for receiving a raw impedance signal, wherein the impedance sensing circuit is configured to produce the intraventricular impedance signal from the raw impedance signal.

* * * * *